United States Patent
Bassilana et al.

(10) Patent No.: US 10,203,327 B2
(45) Date of Patent: Feb. 12, 2019

(54) ORGANIC COMPOUNDS

(71) Applicants: Frederic Bassilana, Basel (CH); Birgit Uta Baumgarten, Riehen (CH); Nathalie Marie-Therese Carte, Huningue (FR); Michel Detheux, Mignault (BE); Rocco Falchetto, Basel (CH); Sebastien Hannedouche, Temploux (BE); Vincent Lannoy, Liernu (BE); Keith Mansfield, Shrewsbury, MA (US); Klaus Peter Seuwen, Michelbach le Bas (FR); Thomas Laurent Henri Suply, Zimmersheim (FR)

(72) Inventors: Frederic Bassilana, Basel (CH); Birgit Uta Baumgarten, Riehen (CH); Nathalie Marie-Therese Carte, Huningue (FR); Michel Detheux, Mignault (BE); Rocco Falchetto, Basel (CH); Sebastien Hannedouche, Temploux (BE); Vincent Lannoy, Liernu (BE); Keith Mansfield, Shrewsbury, MA (US); Klaus Peter Seuwen, Michelbach le Bas (FR); Thomas Laurent Henri Suply, Zimmersheim (FR)

(73) Assignees: Novartis AG, Basel (CH); Odega S.A., Gosselies (BE)

( * ) Notice: Subject to any disclaimer, the term of this patent is extended or adjusted under 35 U.S.C. 154(b) by 125 days.

(21) Appl. No.: 15/034,721

(22) PCT Filed: Oct. 23, 2014

(86) PCT No.: PCT/US2014/061868
§ 371 (c)(1),
(2) Date: May 5, 2016

(87) PCT Pub. No.: WO2015/069459
PCT Pub. Date: May 14, 2015

(65) Prior Publication Data
US 2016/0274110 A1 Sep. 22, 2016

Related U.S. Application Data

(60) Provisional application No. 61/899,978, filed on Nov. 5, 2013.

(51) Int. Cl.
*C07K 16/28* (2006.01)
*G01N 33/566* (2006.01)

(52) U.S. Cl.
CPC .......... *G01N 33/566* (2013.01); *C07K 16/28* (2013.01); *G01N 2333/4719* (2013.01)

(58) Field of Classification Search
CPC ......... G01N 33/566; G01N 2333/4719; C07K 16/28
See application file for complete search history.

(56) References Cited

FOREIGN PATENT DOCUMENTS

| WO | 01/98497 A1 | 12/2001 |
|---|---|---|
| WO | 03/037251 A2 | 5/2003 |
| WO | 2005/040823 A1 | 5/2005 |

OTHER PUBLICATIONS

Ocon et al., A Mucosal and Cutaneous Chemokine Ligand for the Lymphocyte Chemoattractant Receptor GPR15. Front Immunol. 8 : 1111, 2017.*
Suply et al., A natural ligand for the orphan receptor GPR15 modulates lymphocyte recruitment to epithelia. Sci Signal. 12;10(496), 2017 (Abstract).*
Cartwright et al., "Orphan receptor GPR15/BOB is up-regulated in rheumatoid arthritis", Cytokine, 67(2):53-59 2014.
Gudjonsson et al., "Global Gene Expression Analysis Reveals Evidence for Decreased Lipid Biosynthesis and Increased Innate Immunity in Uninvolved Psoriatic Skin", Journal of Investigative Dermatology, 129(12):2795-2804 2009.
Hueber et al., "Effects of AIN457, a Fully Human Antibody to Interleukin-17A, on Psoriasis, Rheumatoid Arthritis, and Uveitis", Science Translation Medicine, American Association for the Advancement of Science, US, 2(52):1-9 2010.
Kim et al., "GPR15-Mediated Homing Controls Immune Homeostasis in the Large Intestine Mucosa", Science, 340(6139):1456-1459 2013.
Pan et al., "CSBF/C10orf99, a novel potential cytokine, inhibits colon cancer cell growth through inducing G1 arrest", Scientific Reports, 4(6812) 1-11 2014.

* cited by examiner

*Primary Examiner* — Ruixiang Li
(74) *Attorney, Agent, or Firm* — Kun Wang; Genomics Institute of the Novartis Research Foundation

(57) ABSTRACT

The present invention relates to modulators of the interaction between G-protein coupled receptor 15(GPR15) and c10orf99. The modulator may be a small chemical molecule, antibody or other therapeutic protein. Methods of medical treatment and methods of identifying modulators are also described.

5 Claims, 8 Drawing Sheets
Specification includes a Sequence Listing.

SEQUENCE LISTING

```
<160> NUMBER OF SEQ ID NOS: 11

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 1

Arg Arg His Pro Arg Asn Pro Ala Lys Xaa Gly Lys Ile Xaa Ile
1               5                   10                  15

<210> SEQ ID NO 2
<211> LENGTH: 15
```

```
<212> TYPE: PRT
<213> ORGANISM: Sus scrofa

<400> SEQUENCE: 2

Gln Lys Pro Gln Leu Trp Val Val Pro Gly Ala Leu Pro Gln Val
1               5                   10                  15

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Pro Gly Pro Asp Leu Met Pro Gln Lys
1               5                   10

<210> SEQ ID NO 4
<211> LENGTH: 57
<212> TYPE: PRT
<213> ORGANISM: Sus scrofa

<400> SEQUENCE: 4

Arg Arg His Pro Arg Asn Pro Ala Lys Pro Gly Lys Ile Arg Ile Cys
1               5                   10                  15

Cys Pro Arg Leu Pro Gly Pro Asp Leu Met Pro Gln Lys Gly His His
            20                  25                  30

Met Arg Ile Cys Arg Pro Cys Lys Phe Lys Gln Lys Pro Gln Leu Trp
        35                  40                  45

Val Val Pro Gly Ala Leu Pro Gln Val
    50                  55

<210> SEQ ID NO 5
<211> LENGTH: 81
<212> TYPE: PRT
<213> ORGANISM: Homo sapiens

<400> SEQUENCE: 5

Met Arg Leu Leu Val Leu Ser Ser Leu Leu Cys Ile Leu Leu Leu Cys
1               5                   10                  15

Phe Ser Ile Phe Ser Thr Glu Gly Lys Arg Arg Pro Ala Lys Ala Trp
            20                  25                  30

Ser Gly Arg Arg Thr Arg Leu Cys Cys His Arg Val Pro Ser Pro Asn
        35                  40                  45

Ser Thr Asn Leu Lys Gly His His Val Arg Leu Cys Lys Pro Cys Lys
    50                  55                  60

Leu Glu Pro Glu Pro Arg Leu Trp Val Val Pro Gly Ala Leu Pro Gln
65                  70                  75                  80

Val

<210> SEQ ID NO 6
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Arg Arg Pro Ala Lys Ala Trp Ser Gly Arg Arg Thr Arg Leu Cys
```

```
                1               5                   10                  15
Cys His Arg Val Pro Ser Pro Asn Ser Thr Asn Leu Lys Gly His His
                    20                  25                  30

Val Arg Leu Cys Lys Pro Cys Lys Leu Glu Pro Glu Pro Arg Leu Trp
            35                  40                  45

Val Val Pro Gly Ala Leu Pro Gln Val
        50                  55
```

<210> SEQ ID NO 7
<211> LENGTH: 77
<212> TYPE: PRT
<213> ORGANISM: Rattus norvegicus

<400> SEQUENCE: 7

```
Met Arg Leu Leu Thr Leu Ser Gly Leu Phe Phe Met Leu Phe Leu Cys
1               5                   10                  15

Leu Cys Val Leu Ser Ser Glu Gly Arg Lys Arg Pro Ala Lys Phe Pro
                    20                  25                  30

Lys Leu Arg Pro Cys Cys His Leu Ser Pro Arg Ser Lys Pro Ile Thr
            35                  40                  45

Trp Lys Gly Asn His Thr Arg Pro Cys Arg Pro Cys Arg Lys Leu Glu
        50                  55                  60

Ser Asn Ser Trp Val Val Pro Gly Ala Leu Pro Gln Ile
65                  70                  75
```

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
His His His His His
1               5
```

<210> SEQ ID NO 9
<211> LENGTH: 360
<212> TYPE: PRT
<213> ORGANISM: Homo sapiens

<400> SEQUENCE: 9

```
Met Asp Pro Glu Glu Thr Ser Val Tyr Leu Asp Tyr Tyr Ala Thr
1               5                   10                  15

Ser Pro Asn Ser Asp Ile Arg Glu Thr His Ser His Val Pro Tyr Thr
                    20                  25                  30

Ser Val Phe Leu Pro Val Phe Tyr Thr Ala Val Phe Leu Thr Gly Val
            35                  40                  45

Leu Gly Asn Leu Val Leu Met Gly Ala Leu His Phe Lys Pro Gly Ser
        50                  55                  60

Arg Arg Leu Ile Asp Ile Phe Ile Ile Asn Leu Ala Ala Ser Asp Phe
65                  70                  75                  80

Ile Phe Leu Val Thr Leu Pro Leu Trp Val Asp Lys Glu Ala Ser Leu
                85                  90                  95

Gly Leu Trp Arg Thr Gly Ser Phe Leu Cys Lys Gly Ser Ser Tyr Met
            100                 105                 110

Ile Ser Val Asn Met His Cys Ser Val Leu Leu Leu Thr Cys Met Ser
        115                 120                 125
```

Val Asp Arg Tyr Leu Ala Ile Val Trp Pro Val Ser Arg Lys Phe
            130                 135                 140

Arg Arg Thr Asp Cys Ala Tyr Val Val Cys Ala Ser Ile Trp Phe Ile
145                 150                 155                 160

Ser Cys Leu Leu Gly Leu Pro Thr Leu Leu Ser Arg Glu Leu Thr Leu
                165                 170                 175

Ile Asp Asp Lys Pro Tyr Cys Ala Glu Lys Lys Ala Thr Pro Ile Lys
                180                 185                 190

Leu Ile Trp Ser Leu Val Ala Leu Ile Phe Thr Phe Val Pro Leu
            195                 200                 205

Leu Ser Ile Val Thr Cys Tyr Cys Cys Ile Ala Arg Lys Leu Cys Ala
    210                 215                 220

His Tyr Gln Gln Ser Gly Lys His Asn Lys Lys Leu Lys Lys Ser Ile
225                 230                 235                 240

Lys Ile Ile Phe Ile Val Val Ala Ala Phe Leu Val Ser Trp Leu Pro
                245                 250                 255

Phe Asn Thr Phe Lys Phe Leu Ala Ile Val Ser Gly Leu Arg Gln Glu
                260                 265                 270

His Tyr Leu Pro Ser Ala Ile Leu Gln Leu Gly Met Glu Val Ser Gly
            275                 280                 285

Pro Leu Ala Phe Ala Asn Ser Cys Val Asn Pro Phe Ile Tyr Tyr Ile
            290                 295                 300

Phe Asp Ser Tyr Ile Arg Arg Ala Ile Val His Cys Leu Cys Pro Cys
305                 310                 315                 320

Leu Lys Asn Tyr Asp Phe Gly Ser Ser Thr Glu Thr Ser Asp Ser His
                325                 330                 335

Leu Thr Lys Ala Leu Ser Thr Phe Ile His Ala Glu Asp Phe Ala Arg
            340                 345                 350

Arg Arg Lys Arg Ser Val Ser Leu
            355                 360

<210> SEQ ID NO 10
<211> LENGTH: 360
<212> TYPE: PRT
<213> ORGANISM: Rattus norvegicus

<400> SEQUENCE: 10

Met Glu Pro Ala Thr Thr Leu Phe Tyr Leu Asp Tyr Tyr Asp Ala Thr
1               5                   10                  15

Ser Pro Asp Pro Arg Ile Met Glu Thr Pro Ser His Thr Ser Tyr Thr
                20                  25                  30

Ser Val Phe Leu Pro Val Phe Tyr Thr Ala Val Phe Leu Thr Gly Val
            35                  40                  45

Leu Gly Asn Phe Ile Leu Met Val Thr Leu His Phe Lys His Arg Asn
    50                  55                  60

Arg Arg Leu Ile Asp Ile Phe Ile Ile Asn Leu Ala Ala Ser Asp Phe
65                  70                  75                  80

Ile Phe Leu Val Thr Leu Pro Leu Trp Val Asp Lys Glu Ala Ser Leu
                85                  90                  95

Gly Leu Trp Arg Thr Gly Ser Leu Leu Cys Lys Gly Ser Ser Tyr Thr
            100                 105                 110

Ile Ser Val Asn Met His Cys Asn Val Phe Leu Leu Thr Cys Met Ser
    115                 120                 125

Met Asp Arg Tyr Leu Ala Ile Met Arg Pro Thr Leu Ala Arg Arg Leu

```
        130                 135                 140
Arg Arg Arg Ser Cys Ala Tyr Ala Val Cys Ala Val Ile Trp Ile Ile
145                 150                 155                 160

Ser Cys Leu Leu Gly Leu Pro Thr Leu Leu Ser Arg Gly Leu Thr His
                    165                 170                 175

Ile Glu Gly Lys Pro Tyr Cys Ala Glu Lys Lys Pro Thr Ser Leu Lys
                180                 185                 190

Leu Met Trp Gly Leu Val Ala Leu Ile Ala Thr Phe Phe Val Pro Leu
                195                 200                 205

Leu Ser Ile Val Ser Ser Tyr Cys Cys Ile Thr Arg Arg Leu Cys Ala
            210                 215                 220

His Tyr Gln Gln Ser Gly Lys His Asn Lys Lys Leu Arg Lys Ser Ile
225                 230                 235                 240

Lys Ile Ile Val Ile Val Ala Ala Phe Thr Ile Ser Trp Val Pro
                    245                 250                 255

Phe Asn Thr Val Lys Leu Leu Ala Ile Val Ser Gly Leu Gln Pro Glu
                260                 265                 270

Ser Gln Phe Pro Ser Glu Ser Leu Gln Gln Ala Met Lys Val Thr Gly
                275                 280                 285

Ser Leu Ala Phe Ala Asn Ser Cys Val Asn Pro Leu Leu Tyr Tyr Ile
                290                 295                 300

Phe Asp Ser Tyr Ile Arg Arg Ala Ile Val Arg Ser Leu Cys Pro Cys
305                 310                 315                 320

Leu Lys Ile His Asn Ile Gly Ser Ser Thr Glu Thr Leu Asp Ser His
                    325                 330                 335

Leu Thr Lys Ala Leu Ala Asn Phe Ile His Ser Glu Asp Phe Val Lys
                340                 345                 350

Arg Arg Lys Arg Ser Val Ser Leu
                355                 360

<210> SEQ ID NO 11
<211> LENGTH: 360
<212> TYPE: PRT
<213> ORGANISM: Mus musculus

<400> SEQUENCE: 11

Met Glu Pro Ala Thr Ala Leu Leu Ile Val Asp Tyr Tyr Asp Tyr Thr
1               5                   10                  15

Ser Pro Asp Pro Pro Phe Leu Glu Thr Pro Ser His Leu Ser Tyr Thr
                20                  25                  30

Ser Val Phe Leu Pro Ile Phe Tyr Thr Val Val Phe Leu Thr Gly Val
                35                  40                  45

Val Gly Asn Phe Ile Leu Met Ile Ala Leu His Phe Lys Arg Gly Asn
            50                  55                  60

Arg Arg Leu Ile Asp Ile Phe Ile Ile Asn Leu Ala Ala Ser Asp Phe
65                  70                  75                  80

Ile Phe Leu Val Thr Val Pro Leu Trp Met Asp Lys Glu Ala Ser Leu
                85                  90                  95

Gly Leu Trp Arg Thr Gly Ser Phe Leu Cys Lys Gly Ser Ser Tyr Val
                100                 105                 110

Ile Ser Val Asn Met His Cys Ser Val Phe Leu Leu Thr Cys Met Ser
            115                 120                 125

Met Asp Arg Tyr Leu Ala Ile Met His Pro Ala Leu Ala Lys Arg Leu
            130                 135                 140
```

```
Arg Arg Arg Ser Ser Ala Tyr Ala Val Cys Ala Val Val Trp Ile Ile
145                 150                 155                 160

Ser Cys Val Leu Gly Leu Pro Thr Leu Leu Ser Arg Glu Leu Thr His
            165                 170                 175

Ile Glu Gly Lys Pro Tyr Cys Ala Glu Lys Lys Pro Thr Ser Leu Lys
            180                 185                 190

Leu Met Trp Gly Leu Val Ala Leu Ile Thr Thr Phe Phe Val Pro Leu
        195                 200                 205

Leu Ser Ile Val Thr Cys Tyr Cys Cys Ile Thr Arg Arg Leu Cys Ala
        210                 215                 220

His Tyr Gln Gln Ser Gly Lys His Asn Lys Lys Leu Lys Lys Ser Ile
225                 230                 235                 240

Lys Ile Val Ile Ile Ala Val Ala Ala Phe Thr Val Ser Trp Val Pro
                245                 250                 255

Phe Asn Thr Phe Lys Leu Leu Ala Ile Val Ser Gly Phe Gln Pro Glu
                260                 265                 270

Gly Leu Phe His Ser Glu Ala Leu Gln Leu Ala Met Asn Val Thr Gly
            275                 280                 285

Pro Leu Ala Phe Ala Ser Ser Cys Val Asn Pro Leu Ile Tyr Tyr Val
        290                 295                 300

Phe Asp Ser Tyr Ile Arg Arg Ala Ile Val Arg Cys Leu Cys Pro Cys
305                 310                 315                 320

Leu Lys Thr His Asn Phe Gly Ser Ser Thr Glu Thr Ser Asp Ser His
                325                 330                 335

Leu Thr Lys Ala Leu Ser Asn Phe Ile His Ala Glu Asp Phe Ile Arg
            340                 345                 350

Arg Arg Lys Arg Ser Val Ser Leu
            355                 360
```

ORGANIC COMPOUNDS

SEQUENCE LISTING

The instant application contains a Sequence Listing which has been submitted electronically in ASCII format and is hereby incorporated by reference in its entirety. Said ASCII copy, created on Aug. 23, 2018, is named PAT054709-US-PCT_SL.txt and is 13,541 bytes in size.

FIELD OF THE INVENTION

The present invention relates to modulators, particularly inhibitors, of the interaction between c10orf99 polypeptide ("c10orf99") and G-protein coupled receptor 15 ("GPR15"). More particularly the present invention relates to pharmaceutical compositions comprising said modulators and methods of treating diseases or disorders responsive to modulating said interaction. Other aspects, objects and advantages of the present invention will be apparent from the description below.

BACKGROUND OF THE INVENTION

The G Protein-Coupled Receptor 15 (GPR15), also called BOB (Brother Of Bonzo), belongs to the superfamily of Rhodopsin-like 7TM receptors (seven transmembrane domain receptors) also known as G-protein coupled receptors (GPCRs). GPR15 is an orphan G protein coupled receptor for which no ligand is known. GPR15 was cloned in 1995 using degenerate oligonucleotide primers based on highly conserved regions in TM3 of the opioid-like genes GPR7 and GPR8 (Heiber, M., et al. (1996) Genomics 32, 462-65).

The GPR15 gene is localized to chromosome 3q11.2-q13.1, and its closest homolog is the orphan GPR25, with 32% identity. Other receptors like the Apelin and the Angiotensin receptors share roughly 30% homology with GPR15 (Fredricksson, et al. (2003) Molecular Pharmacology, Vol. 63(6), 1256-72). GPR15 is also homologous to the interleukin 8b receptor and to chemokine receptors; although the protein lacks several hallmarks of chemokine receptors, it shares an amino-terminal motif rich in tyrosine residues with at least with CCR5 (Farzan, et al. (1997) Journal of Experimental Medicine, Vol. 186(3): 405-11).

The GPR15 ligand and receptor system ("GPR15 L/R system") is involved in maintaining intestinal epithelium homeostasis. GPR15 expression was detected in the GI tract in the mucosa of the gut as well as in the HT29 cell line (Clayton, et al. (2001) Am J Pathol, 159(5), 1933-9) and on lymphocytes (see, e.g., PCT publication WO2005/040823, assigned to Bayer Healthcare AG).

GPR15 is expressed in human CD4(+) T lymphocytes and activated rhesus macaque peripheral blood mononuclear cells, and in regulatory T cells (Tregs). Recently GPR15 was claimed as involved in Treg homing toward the lamina propria of the large intestine, a tissue where we know the GPR15 ligand ("GPR15L") is highly expressed (Kim, et al. (2013) Science. June 21; 340(6139)).

The GPR15 L/R system has been implicated in a variety of pathologic conditions in the literature. By way of non-limiting examples:

(1) Lack of GPR15 results in severe body weight loss with increased inflammation and tissue damage in the Citrobacterrodentium infection-induced Inflammatory Bowel Disease (IBD) mouse model (Kim et al. (2013) Science 340 (6139):1456-9).

(2) GPR15L is up-regulated in human skin transplantation and mouse skin wound healing models suggesting a role of GPR15L/R system in reducing inflammation or triggering (re-)epithelialization mechanisms. In addition, GPR15L is strongly expressed in skin lesions of psoriatic patients (Gudjonsson et al. (2009) Journal of Investigative Dermatology Vol. 129(12): 2795-2804). Treatment by AIN-457 decreases GPR15L expression in correlation with amelioration of the PASI (Hueber, et al. (2010) Sci Transl Med. Vol. 2(52), 52ra72).

(3) GPR15 locus methylation is significantly associated with smoking behaviour (Sun, et al. (2013) Hum Genet, Vol. 132(6), 1027-1037)(Wan, et al. (2012) Hum Mol Genet Vol. 21(13), 3073-82); and the rs1675521 A allele is associated with an increased asthma exacerbation (p=0.007) (Sharma, et al. (2011) Congress ATS 2011 Abstract 19595). GPR15L methylation and expression in the oral mucosa is significantly associated with smoking behavior (Boyle J O, et al. Cancer Pre Res Vol. 3(3), 266-78). These data suggest a role of the GPR15L/R system in the maintenance of the lung epithelium homeostasis in a disease context.

In addition, GPR15 is differentially expressed in rheumatoid arthritis (RA) and non-RA synovial tissue. RNA was present in RA monocytes/macrophages, and protein was expressed by monocytes/macrophages and neutrophils in which levels were higher in RA than in normal peripheral blood (Cartwright, et al. (2010) Rheumatology, 49: i43-i45).

GPR15 is, among other GPCRs such as CCR5, CXCR4, CCR3, CCR2b, CCRB, CXCR6, GPR1, CX3CR1, a co-receptor utilized by HIV and related viruses to infect target cells. In this context, GPR15 has been implicated as mediating gp120-induced calcium signalling and microtubule loss in HT-29 cells (a human colon colorectal adenocarcinoma cell line). These calcium and microtubule changes were previously shown to induce enteropathy-like malabsorption and increased paracellular permeability associated with HIV infection; it has therefore been postulated that gp120-induced GPR15 activation causes HIV enteropathy (Clayton, et al. (2001) Am J Pathol, 159(5), 1933-9).

External publications describe the relationship between Epstein-Barr Virus infection and consequent GPR15 expression and/or promoter methylation (Caliskan, et al. (2011) Hum Mol Genet, Vol. 20(8), 1643-52; Hernando, et al. (2013) Genome Biol Vol. 14(1):R3; Matsusaka, et al. (2011) Cancer Res Vol. 71(23):7187-97.

SUMMARY OF THE INVENTION

The present invention is based, at least in part, on the discovery that c10orf99 is a ligand for GPR15 (i.e., c10orf99 is "GPR15L"). The ligand was purified from porcine aqueous colon extracts and identified by mass spectrometry analysis. As described herein, the peptide was synthesized, produced in larger quantities through recombinant expression or chemical synthesis, and then purified and quantified. Experimental verification procedures led to confirmation of the GPR15 ligand as the c10orf99 polypeptide, a high affinity natural agonist with $EC_{50}$ value below 10 nM, as seen for instance in several in vitro cellular assays, including an aequorin assay, using cAMP in CHO-GPR15 cell line, and in a HEK-GPR15 cell line.

In accordance with a first aspect of the present invention there is provided a modulator (e.g., an antagonist/inhibitor or an agonist/enhancer) of the interaction between c10orf99 and GPR15.

In some embodiments of the invention, the modulator is an inhibitor that binds with c10orf99 and/or GPR15 and inhibits the interaction between the ligand and receptor. The inhibitor may be a therapeutic protein, such as an antibody or antibody fragment, or a small molecule chemical entity. Said inhibitor can inhibit the expression of c10orf99 and/or GPR15 alone or can work to prevent the pair from interacting with one another.

Further, in other embodiments the modulator is an inhibitor of GPR15 expression. Such inhibitors may be an anti-sense oligonucleotide comprising or consisting essentially of a sequence (a) capable of forming a stable triplex with a portion of the GPR15 gene, or (b) capable of forming a stable duplex with a portion of an mRNA transcript of the GPR15 gene under physiological conditions. Alternatively, or in addition, the inhibitor may be a short-interfering RNA (siRNA) molecule capable of interfering with the translation of the GPR15 transcript.

Further, in other embodiments the modulator is an inhibitor of c10orf99 expression. Such inhibitors may be an anti-sense oligonucleotide comprising or consisting essentially of a sequence (a) capable of forming a stable triplex with a portion of the c10orf99 gene, or (b) capable of forming a stable duplex with a portion of an mRNA transcript of the c10orf99 gene under physiological conditions. Alternatively, or in addition, the inhibitor may be a short-interfering RNA (siRNA) molecule capable of interfering with the translation of the c10orf99 transcript.

In some embodiments of the invention, the modulator is an enhancer or agonist that binds with c10orf99 and/or GPR15 and facilitates or increases the interaction between the ligand and receptor (e.g., the rate and/or efficiency of the interaction between the pair). The agonist may be a therapeutic protein, such as an antibody or antibody fragment, or a small molecule chemical entity. Said agonist can upregulate the expression of c10orf99 and/or GPR15 alone or can work to facilitate the way the pair interacts together.

In another aspect of the invention there is provided a pharmaceutical composition comprising a modulator of the first aspect, supra, together with a pharmaceutically acceptable carrier or diluent.

In yet another aspect of the invention there is provided a method of treating a mammalian subject, particularly a human subject afflicted with a disease or disorder responsive to modulation of the interaction between c10orf99 and GPR15, which method comprises administering a therapeutically effective amount of the pharmaceutical aspect of the second aspect, supra.

In another aspect there is provided a process for the manufacture of a modulator of the first and a pharmaceutical composition of the second aspect, supra.

In yet another aspect of the invention, there is provided a method of identifying a modulator of the interaction between c10orf99 and GPR15, which method comprises contacting c10orf99 and/or GPR15 with a candidate modulator and observing the candidate's effect on the interaction between ligand and receptor.

The invention further encompasses the use of the interaction of GPR15 and c10orf99 1-57 as the basis of screening assays for agents that modulate the activity of GPR15.

The invention encompasses a method of identifying an agent that modulates the interaction between c10orf99 1-57 and GPR15, said method comprising: a) contacting GPR15 with c10orf99 1-57 in the presence and absence of a candidate modulator under conditions permitting the binding of c10orf99 1-57 to GPR15; and b) measuring the binding of GPR15 to c10orf99 1-57, wherein a decrease in binding in the presence of the candidate modulator, relative to the binding in the absence of the candidate modulator, identifies the candidate modulator as an agent that modulates the function of GPR15.

The invention further encompasses a method of identifying an agent that modulates the function of GPR15, said method comprising: a) contacting GPR15 with c10orf99 1-57 in the presence and absence of a candidate modulator; and b) measuring a signaling activity of GPR15, wherein a change in the activity in the presence of the candidate modulator relative to the activity in the absence of the candidate modulator identifies the candidate modulator as an agent that modulates the function of GPR15.

The invention further encompasses a method of identifying an agent that modulates the function of GPR15, said method comprising: a) contacting GPR15 with a candidate modulator; b) measuring a signaling activity of GPR15 in the presence of the candidate modulator; and c) comparing the activity measured in the presence of the candidate modulator to the activity measured in a sample in which the GPR15 is contacted with c10orf99 1-57 at its $EC_{50}$, wherein the candidate modulator is identified as an agent that modulates the function of GPR15 when the amount of the activity measured in the presence of the candidate modulator is at least 50% of the amount induced by c10orf99 1-57 present at its $EC_{50}$.

In a preferred embodiment of each of the preceding methods, c10orf99 1-57 is detectably labeled. It is preferred that c10orf99 1-57 is detectably labeled with a moiety selected from the group consisting of a radioisotope, a fluorophore, a quencher of fluorescence, an enzyme, an affinity tag and an epitope tag.

In one embodiment of any of the preceding methods, the contacting is performed in or on a cell expressing GPR15.

In another embodiment of any of the preceding methods, the method is performed using a membrane fraction from cells expressing GPR15.

In another embodiment, the agent is selected from the group consisting of a peptide, a polypeptide, an antibody or antigen-binding fragment thereof, a lipid, a carbohydrate, a nucleic acid, and a small organic molecule.

In another embodiment, the step of measuring a signaling activity of GPR15 comprises detecting a change in the level of a second messenger.

In another embodiment, the step of measuring a signaling activity comprises measurement of guanine nucleotide binding or exchange, adenylatecyclase activity, cAMP, Protein Kinase C activity, phosphatidylinositol breakdown, diacylglycerol, inositol triphosphate, intracellular calcium, arachinoid acid, MAP kinase activity, tyrosine kinase activity, or reporter gene expression.

The invention further encompasses a method of modulating the activity of GPR15 in a cell, the method comprising the step of delivering to the cell an agent that modulates the activity of GPR15, such that the activity of GPR15 is modulated.

DETAILED DESCRIPTION OF THE INVENTION

Figure 1:
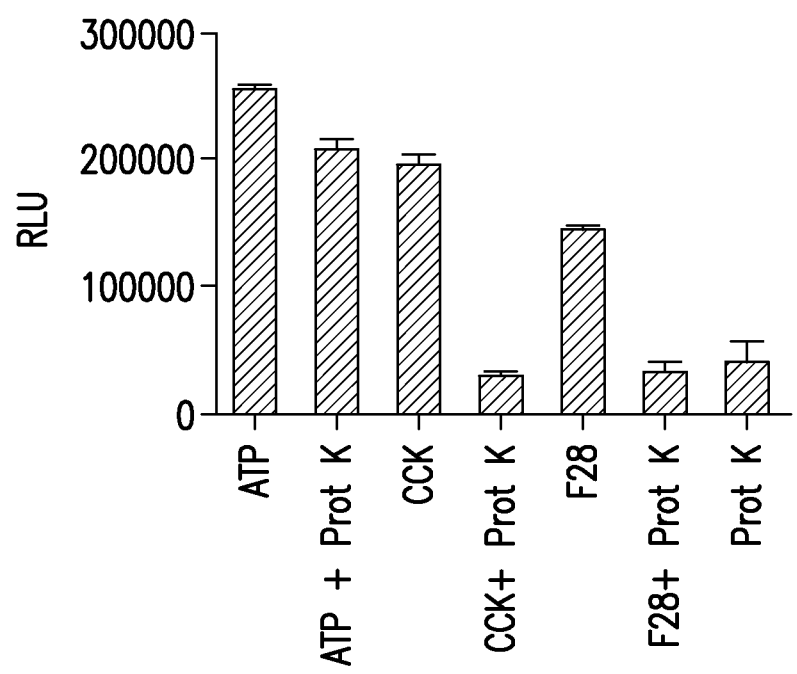
FIG. 1: A graphical depiction showing proteinase K sensitivity of an active GPR15 fraction (F28). The GPR15 active colon fraction is both treated with proteinase K and untreated.

Throughout this specification, the term "c10orf99" refers to human c10orf99 unless otherwise specified. Furthermore, the terms "GPR15L," and "GPR15 ligand" are used interchangeably with "c10orf99," to indicate the ligand for GPR15. Human c10orf99 (hc10orf99; SEQ ID NO:5), includes a signal sequence (amino acids 1-24). The active human c10orf99 peptide (SEQ ID NO: 6) is also referred to as "human 1-57 c10orf99" and "c10orf99 1-57." Therapeutic proteins, polynucleotides and oligonucleotides as described herein are in isolated form. Reference in this specification to "GPR15" refers to human GPR15 unless otherwise specified; likewise, reference to diseases or disorders refers to human diseases or disorders. GPR15 and c10orf99 sequences can be found in the literature as follows (Table 1):

TABLE 1

GPR15 and c10orf99 Sequences

| | GPR15 | | | GPR15L (C10orf99 in man) | |
|---|---|---|---|---|---|
| Species | Ref Seq mRNA | Ref Seq Protein | Species | Ref Seq mRNA | Ref Seq Protein |
| Human | NM_005290 | NP_005281 (SEQ ID NO: 9) | Human | NM_207373 | NP_997256 |
| Rat | NM_001105890 | NP_001099360 (SEQ ID NO: 10) | Rat | NM_001106063 | Wrong frame* |
| Mouse | NM_001162955 | NP_001156427 (SEQ ID NO: 11) | Mouse | XM_980662 | XP_985756 |
| Pig | N/A | N/A | Pig | XM_003133093 | Frame + 3 (114-359) |

* Corrected sequence.
The rat GPR15L sequence, according to NM_001106063, 53-286 Frame + 2, is:
MRLLTLSGLF FMLFLCLCVL SSEGRKRPAK FPKLRPCCHL SPRSKPITWK GNHTRPCRPC RKLESNSWVV PGALPQI (SEQ ID NO: 7)

As used herein, the term "GPR15" also refers to a polypeptide having two essential properties: 1) GPR15 has at least 70% amino acid identity, and preferably 80%, 90%, 95% or higher, including 100% amino acid identity, to RefSeq Protein accession number mentioned in the Table 1; and 2) GPR15 has GPR15 activity, i.e., the polypeptide binds a c10orf99 1-57 or a functional fragment thereof. Optimally, "GPR15" also has GPR15 signaling activity as defined herein.

The term "c10orf99 1-57" also refers to a polypeptide having at least 70% or higher identity to either SEQ ID NO: 6 and the defined polypeptide specifically binds to and activates a signaling activity of GPR15. Preferably, the polypeptide is at least 75%, or higher identity to either SEQ ID NO: 6. Preferably, the polypeptide is at least 80%, or 85%, or 90%, or 95% or higher identity to either SEQ ID NO: 6.

The term "c10orf99 1-57" also refers to a fragment of a polypeptide meeting the preceding definition, wherein the fragment retains at least 50% of the binding activity and level of signaling activation of the full length polypeptide of SEQ ID NO: 6. A c10orf99 1-57 can comprise additions, insertions, deletions or substitutions relative to SEQ ID NO: 6, as long as the resulting polypeptide retains at least 50% of the binding activity and level of signaling activation of the full length polypeptide represented by SEQ ID NO: 6. In addition to the sequences necessary for binding to GPR15 and activating GPR15 signaling activity, c10orf99 1-57, including the truncated c10orf99 1-57, can comprise additional sequences, as in for example, a c10orf99 1-57 fusion protein. Non-limiting examples of fusion partners include glutathione-S-transferase (GST), maltose binding protein, alkaline phosphatase, thioredoxin, green fluorescent protein (GFP), histidine tags (e.g., 6× or greater His), or epitope tags (e.g., Myc tag, FLAG tag).

Throughout this specification, the term "a human disease or disorder responsive to the modulation of the interaction between C10orf99 with GPR15," "a C10orf99: GPR15 related disorder," and the like means conditions that are amenable to therapeutic treatment by modulation of the interaction between C10orf99 and GPR15, e.g., treatment by disruption of the interaction between C10orf99 and GPR15, or treatment by preventing C10orf99 or GPR15 from binding to its cognate receptor or ligand.

Alternately, "C10orf99: GPR15 related disorder" and the like means conditions that are amenable to therapeutic treatment by modulation of the interaction between C10orf99 and GPR15, e.g., treatment by enhancement of the interaction between C10orf99 and GPR15. Non-limiting examples of such diseases include HIV infection and associated pathologies such as enteropathy-like malabsorption and increased paracellular permeability; psoriasis, dermatitis, and other skin disorders such as sarcoidosis and subcorneal pustular dermatosis (also known as Sneddon-Wilkinson disease); colon cancer; uveitis, asthma, chronic obstructive pulmonary disease (COPD); idiopathic pulmonary fibrosis (IPF); diseases with alteration of the epithelial function/structure (e.g., wound healing, skin inflammation, mucositis, inflammatory bowel disease (IBD), lung diseases, rheumatoid arthritis and other autoimmune diseases); metabolic or lipid metabolism disorders; Crohn's disease and colitis; and mild to moderate lymphoid atrophy or hypoplasia and other immune conditions.

Throughout this specification, the following abbreviations are used, meaning the full term in parenthesis: Aeq (aequorin); ATP (Adenosine-Tri-Phosphate); CCK (cholecystokinin); CHO (Chinese Hamster Ovary cell line); HTRF (homogeneous time resolved fluorescence); protK (proteinase K); Fk (forskolin); EC50 (Efficacy concentration 50); nM (nanomolar); and cAMP (cyclic Adenosine Mono Phosphate).

Throughout this specification, the term "Aequorin assay" refers to methods for performing high throughput functional screening of GPCRs. Said methods employ recombinant cell lines stably transfected with plasmids encoding apoaequorin, a GPCR of interest and if necessary, a recombinant G protein to redirect the coupling of the GPCR toward calcium signaling. After clonal selection, the best clones are selected on the basis of pharmacological characterization, high signal to background ratio and stability of expression. This method has been developed by Euroscreen SA, 47 Rue Adrienne Bolland, 6041 Gosselies, Belgium.

Aequorin is a photoprotein isolated from luminescent jellyfish (e.g. *Aequorea victoria*), and is comprised of two distinct units: the apoprotein apoaequorin (~22 kDa); and the prosthetic group, coelenterazine, responsible for emission of light.

In the presence of molecular oxygen the two components of aequorin assemble spontaneously, forming the functional protein. Four EF-hand type regions have been identified in the structure of Aequorin and at least 3 of them function as binding sites for $Ca^{+2}$ ions: $Ca^{+2}$ binding to these EF hands triggers a conformational change of the protein, that leads it to oxidize its prosthetic group, coelenterazine, into excited coelenteramide and $CO_2$.

As the excited coelenteramide relaxes to the ground state, blue light (wavelength=469 nm) is emitted and can be measured by a luminometer. Cultured cells expressing the aequorin gene can effectively synthesize aequorin in a stable or transient way, however recombinant expression only yields the apoprotein, therefore it is necessary to add coelenterazine into the culture medium of the cells to obtain a functional protein and subsequently use its blue light emission to measure intracellular $Ca^{2+}$ concentration. Coelenterazine is a hydrophobic molecule, and therefore is easily taken up across the plasma membrane of higher eukaryotes, making aequorin suitable as a $Ca^{2+}$ reporter in mammalian cells.

The term "specifically binds" means that c10orf99 1-57 has an EC50, IC50, or a Kd of 100 nM or less.

As used herein, the term "GPR15 activity" refers to specific binding of c10orf99 1-57 or a functional fragment thereof by a GPR15.

As used herein, the term "GPR15 signaling activity" refers to the initiation or propagation of signaling by GPR15. GPR15 signaling activity is monitored by measuring a detectable step in a signaling cascade by assaying one or more of the following: stimulation of GDP for GTP exchange on a G protein; alteration of adenylatecyclase activity; protein kinase C modulation; phosphatidylinositol breakdown (generating second messengers diacylglycerol, and inositol triphosphate); intracellular calcium flux; activation of MAP kinases; modulation of tyrosine kinases; or modulation of gene or reporter gene activity. A detectable step in a signaling cascade is considered initiated or mediated if the measurable activity is altered by 10% or more above or below a baseline established in the substantial absence of c10orf99 1-57 relative to any of the GPR15 activity assays. The measurable activity can be measured directly, as in, for example, measurement of cAMP or diacylglycerol levels. Alternatively, the measurable activity can be measured indirectly, as in, for example, a reporter gene assay.

As used herein, the terms "candidate compound" and "candidate modulator" refer to a composition being evaluated for the ability to modulate c10orf99 1-57 binding to GPR15 or the ability to modulate an activity of GPR15. Candidate modulators can be natural or synthetic compounds, including, for example, small molecules, compounds contained in extracts of animal, plant, bacterial or fungal cells, as well as conditioned medium from such cells.

As used herein, the term "small molecule" refers to a compound having molecular mass of less than 3000 Daltons, preferably less than 2000 or 1500, still more preferably less than 1000, and most preferably less than 600 Daltons. A "small organic molecule" is a small molecule that comprises carbon.

As used herein, the term "change in binding" or "change in activity" and the equivalent terms "difference in binding" or "difference in activity" refer to an at least 10% increase or decrease in binding, or signaling activity in a given assay.

As used herein, the term "conditions permitting the binding of c10orf99 1-57 to GPR15" refers to conditions of, for example, temperature, salt concentration, pH and protein concentration under which c10orf99 1-57 binds GPR15. Exact binding conditions will vary depending upon the nature of the assay, for example, whether the assay uses viable cells or only membrane fraction of cells. However, because GPR15 is a cell surface protein, and because c10orf99 1-57 is a secreted polypeptide that interacts with GPR15 on the cell surface, favored conditions will generally include physiological salt (90 mM) and pH (about 7.0 to 8.0). Temperatures for binding can vary from 15° C. to 37° C., but will preferably be between room temperature and about 30° C. The concentration of c10orf99 1-57 and GPR15 in a binding reaction will also vary, but will preferably be about 0.1 pM (e.g., in a reaction with radiolabeled tracer c10orf99 1-57, where the concentration is generally below the $K_d$) to 1 µM (e.g., c10orf99 1-57 as competitor). As an example, for a binding assay using GPR15-expressing cells and purified, recombinant, labeled c10orf99 1-57, binding is performed using 0.1 nM labeled c10orf99 1-57, 100 nM cold c10orf99 1-57, and 25,000 cells at 27° C. in 250 µl of a binding buffer consisting of 50 mM HEPES (pH 7.4), 1 mM $CaCl_2$, and 0.5% Fatty acid free BSA.

As used herein, the term "membrane fraction" refers to a preparation of cellular lipid membranes comprising GPR15. As the term is used herein, a "membrane fraction" is distinct from a cellular homogenate, in that at least a portion (i.e., at least 10%, and preferably more) of non-membrane-associated cellular constituents has been removed. The term "membrane associated" refers to those cellular constituents that are either integrated into a lipid membrane or are physically associated with a component that is integrated into a lipid membrane.

As used herein, the term "decrease in binding" refers to a decrease of at least 10% in the binding of c10orf99 1-57 or other agonist to GPR15 as measured in a binding assay used by those skilled in the art. The term "decrease in binding" also refers to a decrease of at least 10% in the amount of binding detected in a given assay with a known or suspected modulator of GPR15 relative to binding detected in an assay lacking that known or suspected modulator.

As used herein, the term "second messenger" refers to a molecule, generated or caused to vary in concentration by the activation of a G-Protein Coupled Receptor that participates in the transduction of a signal from that GPCR. Non-limiting examples of second messengers include cAMP, diacylglycerol, inositol triphosphates and intracellular calcium. The term "change in the level of a second messenger" refers to an increase or decrease of at least 10% in the detected level of a given second messenger relative to the amount detected in an assay performed in the absence of a candidate modulator.

As used herein, the term "binding" refers to the physical association of c10orf99 1-57 with a receptor (e.g., GPR15). As the term is used herein, binding is "specific" if it occurs with an $EC_{50}$ or a $K_d$ of 100 nM or less, generally in the range of 100 nM to 10 pM. For example, binding is specific if the $EC_{50}$ or $K_d$ is 100 nM, 50 nM, 10 nM, 1 nM, 950 pM, 900 pM, 850 pM, 800 pM, 750 pM, 700 pM, 650 pM, 600 pM, 550 pM, 500 pM, 450 pM, 400 pM, 350 pM, 300 pM, 250 pM, 200 pM, 150 pM, 100 pM, 75 pM, 50 pM, 25 pM or 10 pM or less.

As used herein, the term "$EC_{50}$," refers to that concentration of an agent at which a given activity is 50% of the maximum for that GPR15 activity measurable using the same assay. Stated differently, the "$EC_{50}$" is the concentration of agent that gives 50% activation, when 100% activation is set at the amount of activity that does not increase with the addition of more agonist.

As used herein, the term "$IC_{50}$" is the concentration of an antagonist or inverse agonist that reduces the maximal activation of GPR15 by 50%.

As used herein, the term "agent that modulates the function of GPR15" is a molecule or compound that increases or decreases GPR15 activity, including compounds that change the binding of c10orf99 1-57 or other agonists, and/or compounds that change GPR15 downstream signaling activities.

4.1—Therapeutic Proteins

A therapeutic protein of the present invention may be an antibody, Adnectin, Ankyrin, Maxybody/Avimer, Affibody, anticalin, or Affilin.

4.1.1.—Antibodies

Antibodies of the present invention may be in any of a number of formats well known to the skilled person. These formats include intact antibodies, various antibody fragments and other engineered formats as described below. In preferred forms, antibodies of the present invention are provided as a monoclonal population.

4.1.1.1—Intact Antibodies

Intact antibodies include heteromultimeric glycoproteins comprising at least two heavy and two light chains. Aside from IgM, intact antibodies are usually heterotetrameric glycoproteins of approximately 150 KDa, composed of two identical light (L) chains and two identical heavy (H) chains. Typically, each light chain is linked to a heavy chain by one covalent disulfide bond while the number of disulfide linkages between the heavy chains of different immunoglobulin isotypes varies. Each heavy and light chain also has intra-chain disulfide bridges. Each heavy chain has at one end a variable domain (VH) followed by a number of constant regions. Each light chain has a variable domain (VL) and a constant region at its other end; the constant region of the light chain is aligned with the first constant region of the heavy chain and the light chain variable domain is aligned with the variable domain of the heavy chain. The light chains of antibodies from most vertebrate species can be assigned to one of two type called Kappa or Lambda based on the amino acid sequence of the constant region.

Depending on the amino acid sequence of the constant region of their heavy chains, human antibodies can be assigned to five different classes, IgA, IgD, IgE, IgG and IgM. IgG and IgA can be further subdivided into subclasses, IgG1, IgG2, IgG3 and IgG4; and IgA1 and IgA2. Species variants exist with mouse and rat having at least IgG2a, IgG2b. The variable domain of the antibody confers binding specificity upon the antibody with certain regions displaying particular variability called complementarity determining regions (CDRs). The more conserved portions of the variable region are called Framework regions (FR). The variable domains of intact heavy and light chains each comprise four FR connected by three CDRs. The CDRs in each chain are held together in close proximity by the FR regions and with the CDRs from other chain contribute to the formation of the antigen binding site of antibodies. The constant regions are not directly involved in the binding of the antibody to the antigen but exhibit various effector functions such as participation in antibody dependent cell-mediated cytoxicity (ADCC), phagocytosis via binding to Fcγr receptor, half-life/clearance rate via neonatal Fc receptor (FcRn) and complement dependent cytoxicity via the C1q component of the complement cascade.

Thus, in one embodiment of the invention there is provided an intact therapeutic antibody capable of binding c10orf99 and/or GPR15 and inhibiting the interaction between c10orf99 and GPR15. Such antibodies typically have a human constant region of an IgG isotype such as IgG1 or IgG4 and may be human, humanized or chimeric.

4.1.1.1.1 Human Antibodies

Human antibodies may be produced by a number of methods known to those of skill in the art. Human antibodies can be made by the hybridoma method using human myeloma or mouse-human heteromyeloma cells lines see Kozbor J Immunol 133, 3001, (1984) and Brodeur, Monoclonal Antibody Production Techniques and Applications, pp 51-63 (Marcel Dekker Inc, 1987). Alternative methods include the use of phage libraries or transgenic mice both of which utilize human V region repertoires (see Winter G, (1994), Annu. Rev. Immunol. 12, 433-455, Green L L (1999), J. Immunol. Methods 231, 11-23).

Several strains of transgenic mice are now available wherein their mouse immunoglobulin loci has been replaced with human immunoglobulin gene segments (see Tomizuka K, (2000) PNAS 97, 722-727; Fishwild D M (1996) Nature Biotechnol. 14, 845-851. Mendez M J, 1997, Nature Genetics, 15, 146-156). Upon antigen challenge such mice are capable of producing a repertoire of human antibodies from which antibodies of interest can be selected. Of particular note is the Trimera™ system (see Eren R et al, (1988) Immunology 93:154-161) where human lymphocytes are transplanted into irradiated mice, the Selected Lymphocyte Antibody System (SLAM, see Babcook et al, PNAS (1996) 93: 7843-7848) where human (or other species) lymphocytes are effectively put through a massive pooled in vitro antibody generation procedure followed by deconvulated, limiting dilution and selection procedure and the Xenomouse™ (Abgenix Inc). An alternative approach is available from Morphotek, Inc., using the Morphodoma™ technology.

Phage display technology can be used to produce human antibodies (and fragments thereof), see McCafferty; Nature, 348, 552-553 (1990) and Griffiths A D et al (1994) EMBO 13: 3245-3260. According to this technique, antibody V domain genes are cloned in frame into either a major or minor coat of protein gene of a filamentous bacteriophage such as M13 or fd and displayed (usually with the aid of a helper phage) as function antibody fragments on the surface of the phage particle. Selections based on the function properties of the antibody result in selection of the gene encoding the antibody exhibiting these properties.

The phage display technique can be used to select antigen specific antibodies from libraries made from human B cells taken from individuals afflicted with a disease or disorder described above or alternatively from unimmunized human donors (see Marks; J Mol Bio 222, 581-591, 1991). Where an intact human antibody is desired comprising an Fc domain, it is necessary to reclone the phage displayed derived fragment into a mammalian expression vectors comprising the desired constant regions and to establish stable expressing cell lines.

The technique of affinity maturation (Marks; Bio/technol 10, 779-783 (1992)) may be used to provide binding affinity wherein the affinity of the primary human antibody is improved by sequentially replacing the H and L chain V regions with naturally occurring variants and selecting on the basis of improved binding affinities. Variants of this technique such as 'epitope imprinting' are now also available, see WO 93/06213. See also Waterhouse; Nucl Acids Res 21, 2265-2266 (1993).

Thus in one embodiment of the invention there is provided an intact therapeutic antibody capable of binding c10orf99 and/or GPR15 and inhibiting the interaction between c10orf99 and GPR15. In typical embodiments, the intact therapeutic human antibody comprises a constant region of an IgG isotype, e.g. IgG1 or IgG4.

4.1.1.1.2 Chimaeric and Humanised Antibodies

The use of intact non-human antibodies in the treatment of human diseases or disorders carries with it the potential for the now well established problems of immunogenicity, that is the immune system of the subject may recognise the non-human intact antibody as non-self and mount a neutralising response. This is particularly evident upon multiple administration of the non-human antibody to a human subject. Various techniques have been developed over the years to overcome these problems and generally involve reducing the composition of non-human amino acid sequences in the intact antibody whilst retaining the relative ease in obtaining non-human antibodies from an immunised animal, e.g. mouse, rat or rabbit. Broadly two approaches have been used to achieve this.

The first are chimaeric antibodies, which generally comprise a non-human (e.g. rodent such as mouse) variable domain fused to a human constant region. Because the antigen-binding site of an antibody is localised within the variable regions the chimaeric antibody retains its binding affinity for the antigen but acquires the effector functions of the human constant region and are therefore able to perform effector functions such as described supra. Chimeric antibodies are typically produced using recombinant DNA methods. DNA encoding the antibodies (e.g. cDNA) is isolated and sequenced using conventional procedures (e.g. by using oligonucleotide probes that are capable of binding specifically to genes encoding the H and L chains of the antibody of the invention. Hybridoma cells serve as a typical source of such DNA. Once isolated, the DNA is placed into expression vectors which are then transfected into host cells such as E. Coli, COS cells, CHO cells or myeloma cells that do not otherwise produce immunoglobulin protein to obtain synthesis of the antibody. The DNA may be modified by substituting the coding sequence for human L and H chains for the corresponding non-human (e.g. murine) H and L constant regions see e.g. Morrison; PNAS 81, 6851 (1984).

The second approach involves the generation of humanised antibodies wherein the non-human content of the antibody is reduced by humanizing the variable regions. Two techniques for humanisation have gained popularity. The first is humanisation by CDR grafting. CDRs build loops close to the antibody's N-terminus where they form a surface mounted in a scaffold provided by the framework region. Antigen-binding specificity of the antibody is mainly defined by the topography and by the chemical characteristics of its CDR surface. These features are in turn determined by the conformation of the individual CDRs, by the relative disposition of the CDRs, and by the nature and disposition of the side chains of the residues comprising the CDRs. A large decrease in immunogenicity can be achieved by grafting only the CDRs of a non-human (e.g. murine) antibodies ('donor' antibodies) onto human framework ('acceptor framework') and constant regions (see Jones et al (1986) Nature 321, 522-525 and Verhoeyen M et al (1988) Science 239, 1534-1536).

However, CDR grafting per se may not result in the complete retention of antigen-binding properties, and it is frequency found that some framework residues (sometimes referred to as 'backmutations') of the donor antibody need to be preserved in the humanised compound if significant antigen-binding affinity is to be recovered (see Queen C et al (1989) PNAS 86, 10, 029-10, 033, Co, M et al (1991) Nature 351, 501-502). In this case, human V regions showing the greatest sequence homology to the non-human donor antibody are chosen from a database in order to provide the human framework (FR). The selection of human FRs can be made either from human consensus or individual human antibodies. Where necessary, key residues from the donor antibody are substituted into the human acceptor framework to preserve CDR conformations. Computer modelling of the antibody may be used to help identify such structurally important residues, see, e.g., WO99/48523.

Alternatively, humanisation may be achieved by a process of 'veneering.' A statistical analysis of unique human and murine immunoglobulin heavy and light chain variable regions revealed that the precise patterns of exposed residues are different in human and murine antibodies, and most individual surface positions have a strong preference for a small number of different residues (see Padlan E A, et al; (1991) Mol Immunol 28, 489-498 and Pedersen J T et al (1994) J Mol Biol 235; 959-973). Therefore it is possible to reduce the immunogenicity of a non-human Fv by replacing exposed residues in its framework regions that differ from those usually found in human antibodies. Because protein antigenicity may be correlated with surface accessibility, replacement of the surface residues may be sufficient to render the mouse variable region 'invisible' to the human immune system (see also Mark G E et al (1994) in Handbook of Experimental Pharmacology vol 113: The pharmacology of monoclonal Antibodies, Springer-Verlag, pp 105-134). This procedure of humanisation is referred to as 'veneering' because only the surface of the antibody is altered, the supporting residues remain undisturbed.

Thus in one embodiment of the invention there is provided an intact therapeutic humanised antibody capable of binding c10orf99 and/or GPR15 and inhibiting the interaction between c10orf99 and GPR15. In typical embodiments the intact therapeutic human antibody comprises a constant region of an IgG isotype, e.g. IgG1 or IgG4.

4.1.1.1.3 Bispecific Antibodies

A bispecific antibody is an antibody having binding specificities for at least two different epitopes. Methods of making such antibodies are known in the art. Traditionally, the recombinant production of bispecific antibodies is based on the coexpression of two immunoglobulin H chain-L chain pairs, where the two H chains have different binding specificities, (see Millstein et al, Nature 305, 537-539 (1983), WO93/08829 and Traunecker et al, EMBO, 10, 1991, 3655-3659). Because of the random assortment of H and L chains, a potential mixture of ten different antibody structures are produced of which only one has the desired binding specificity. An alternative approach involves fusing the variable domains with the desired binding specificities to heavy chain constant region comprising at least part of the hinge region, CH2 and CH3 regions.

It is preferred to have the CH1 region containing the site necessary for light chain binding present in at least one of the fusions. DNA encoding these fusions and, if desired, the L chain are inserted into separate expression vectors and are then co-transfected into a suitable host organism. It is possible, though, to insert the coding sequences for two or all three chains into one expression vector. In one preferred approach, the bispecific antibody is composed of an H chain with a first binding specificity in one arm and an H-L chain pair, providing a second binding specificity in the other arm, see WO94/04690. Also see Suresh et al, Methods in Enzymology 121, 210, 1986.

In one embodiment of the invention there is provided a bispecific therapeutic antibody wherein at least one binding specificity of said antibody is for c10orf99 and the second specificity is for GPR15. In preferred forms the bispecific antibody comprises a primate, e.g. human antibody of a IgG (e.g. IgG1 or IgG4) isotype.

4.1.1.1.4 Antibody Fragments

In certain embodiments of the invention there is provided therapeutic antibody fragments which modulate (e.g. inhibit) the interaction between c10orf99 and GPR15. Such fragments may be functional antigen binding fragments of intact and/or humanised chimaeric antibodies such as Fab, Fab', F(ab$_1$)2, Fv, ScFv fragments of the antibodies described supra.

Traditionally, such fragments are produced by the proteolytic digestion of intact antibodies by, e.g., papain digestion (see for example WO 94/29348) but may be produced directly from recombinantly transformed host cells. For the production of ScFv, see Bird et al; (1988) Science, 242, 423-426. In addition, antibody fragments may be produced using a variety of engineering techniques as described below.

$F_V$ fragments appear to have lower interaction energy of their two chains than Fab fragments. To stabilise the association of the VH and VL domains, they have been linked with peptides (Bird et al, (1988) Science, 242, 423-426, Huston et al, PNAS, 85, 5879-5883), disulphide bridges (Glockshuber et al, (1990) Biochemistry, 29, 1362-1367) and 'knob in hole' mutations (Zhu et al (1997), Protein Sci., 6, 781-788). ScFv fragments can be produced by methods well known to those skilled in the art (see Whitlow et al (1991), Methods companion Methods Enzymol, 2, 97-105 and Huston et al (1993) Int Rev Immunol 10, 195-217. ScFv may be produced in bacterial cells such as E. Coli but are more preferably produced in eukaryotic cells. One disadvantage of ScFv is the monovalency of the product, which precludes an increased avidity due to polyvalent binding, and their short half-life. Attempts to overcome these problems include bivalent (ScFv')$_2$ produced from ScFv containing an additional C terminal cysteine by chemical coupling (Adams et al (1993) Can Res 53, 4026-4034 and McCartney et al (1995) Protein Eng, 8, 301-314) or by spontaneous site-specific dimerization of ScFv containing an unpaired C terminal cysteine residue (see Kipriyanov, et al. (1995) Cell. Biophys 26, 187-204).

Alternatively, ScFv can be forced to form multimers by shortening the peptide linker to 3 and 12 residues to form 'diabodies' (see Holliger et al PNAS (1993), 90, 6444-6448). Reducing the linker still further can result in ScFV trimers ('triabodies', see Kortt et al (1997) Protein Eng, 10, 423-433) and tetramers ('tetrabodies', see Le Gall et al (1999) FEBS Lett, 453, 164-168). Construction of bialent ScFV compounds can also be achieved by genetic fusion with protein dimerzing motifs to form 'miniantibodies' (see Pack et al (1992) Biochemistry 31, 1579-1584) and 'minibodies' (see Hu et al (1996), Cancer Res. 56, 3055-3061). ScFv-ScFv tandems ((ScFV)2) may also be produced by linking two ScFV units by a third peptide linger, (see Kurucz et al (1995) J Immunol, 154, 4576-4582). Bispecific diabodies can be produced through the noncovalent association of two single chain fusion products consisting of VH domain from one antibody connected by a short linker to the VL domain of another antibody, (see Kipriyanov et al (1998), Int J Can 77, 763-772).

The stability of such bispecific diabodies can be enhanced by the introduction of disulphide bridges or 'knob in hole' mutations as described supra or by the formation of single chain diabodies (ScDb) wherein two hybrid ScFv fragments are connected through a peptide linker (see Kontermann et al (1999) J Immunol Methods 226, 179-188). Tetravalent bispecific compounds are available by e.g. fusing a ScFv fragment to the CH3 domain of an IgG compound or to a Fab fragment through the hinge region (see Coloma et al (1997) Nature Biotechnol, 15, 159-163). Alternatively, tetravalent bispecific compounds have been created by the fusion of bispecific single chain diabodies (see Alt et al (1999) FEBS Lett 454, 90-94). Smaller tetravalent bispecific compounds can also be formed by the dimerization of either ScFv-ScFv tandems with a linker containing a helix-loop-helix motif (DiBimini antibodies, see Muller et al (1998) FEBS Lett 432, 45-49) or a single chain compound comprising four antibody variable domains (VH and VL) in an orientation preventing intramolecular pairing (tandem diabody, see Kipriyanov et al, (1999) J Mol Biol 293, 41-56).

Bispecific Fab'$_2$ fragments can be created by chemical coupling of Fab' fragments or by heterodimerization through leucine zippers (see Shalaby, et al. (1992) J Exp Med 175, 217-225 and Kostelny et al (1992), J Immunol 148 1547-1553). Also available are isolated VH and VL domains (Domantis plc), see U.S. Pat. No. 6,248,516; U.S. Pat. No. 6,291,158; U.S. Pat. No. 6,172,197 and isolated VHH domain antibodies (Nanobodies). These domain and nanobodies may be dual specific having one specificity directed to a half life extending protein such as human serum albumin (HSA). Such domain and nanobodies both monospecific for a NRG1 protein of the invention and further dual specific for a half life extending protein such as HSA are specifically contemplated by the invention.

In one embodiment there is provided a therapeutic antibody fragment (e.g. ScFv, Fab, Fab', F(ab')$_2$) or an engineered antibody fragment as described supra that binds with c10orf99 and/or GPR15 and inhibits the interaction between ligand and receptor.

4.1.1.1.5 Heteroconjugate Antibodies

Heteroconjugate antibodies also form an embodiment of the present invention. Heteroconjugate antibodies are composed of two covalently joined antibodies formed using any convenient cross-linking methods. See, for example, U.S. Pat. No. 4,676,980.

4.1.1.1.6 Other Modifications

The interaction between the Fc region of an antibody and various Fc receptors (FcγR) is believed to mediate the effector functions of the antibody which include antibody-dependent cellular cytotoxicity (ADCC), fixation of complement, phagocytosis, and half-life/clearance of the antibody. Various modifications to the Fc region of antibodies of the invention may be carried out depending on the desired property. For example, specific mutations in the Fc region to render an otherwise lytic antibody, non-lytic is detailed in EP 0629 240B1 and EP 0307 434B2 or one may incorporate a salvage receptor binding epitope into the antibody to increase serum half-life, see U.S. Pat. No. 5,739,277.

There are five currently recognised human Fcγ, FcγR (I), FCγRIIb, FcγRIIIa and neonatal FcRn. Shields et al, (2001) J Biol Chem 276, 6591-6604 demonstrated that a common set of IgG1 residues is involved in binding all FcγRs, while FCγRII and FcγRIII utilize distinct sites outside of this common set. One group of IgG1 residues reduced binding to all FcγRs when altered to alanine: Pro-238, Asp-265, Asp-270, Asn-297 and Pro-239. All are in the IgG CH2 domain and clustered near the hinge joining CH1 and CH2. While FcγRI utilizes only the common set of IgG1 residues for binding, FcγRII and FcγRIII (e.g. Glu-293). Some variants showed improved binding to FcγRII or FcγRIII but did not affect binding to the other receptor (e.g. Ser-267Ala improved binding to FcγRII but binding to FcγRIII was unaffected).

Other variants exhibited improved binding to DcγRII or FcγRIII with reduction in binding to the other receptor (e.g. Ser298Ala improved binding to FcγRIII and reduced binding to FcγRII). For FCγRIIIa, the best binding IgG1 variants had combined alanine substitutions at Ser-298, Glu-333 and Ls-334. The neonatal FcRn receptor is believed to be involved in both antibody clearance and the transcytosis across tissues (see Junghans R P (1997) Immunol Res 16, 2957 and Ghetie et al (2000) Annu Rev Immunol 18, 739-766). Human IgG1 residues determined to interact directly with human FcRn included Ile253, Ser254, Lys288, Thr307, Gln311, Asn434 and His435. Switches at any of these positions described in this section may enable increased serum half-life and/or altered effector properties of antibodies of the invention and therefore forms an embodiment of the invention.

Other modifications include glycosylation variants of the antibodies of the invention. Glycosylation of antibodies at conserved positions in their constant regions is known to have a profound effect on antibody function, particularly effector functioning such as those described above, see for example, Boyd, et al. (1996) Mol Immunol 32, 1311-1318. Glycosylation variants of the therapeutic antibodies or antigen binding fragments thereof of the present invention wherein one or more carbohydrate moiety is added, substituted, deleted or modified are contemplated. Introduction of an asparagine-X-serin or asparagine-X-threonine motif creates a potential side for enzymatic attachment of carbonhydrate moieties and may therefore be used to manipulate the glycosylation of an antibody.

In Raju et al (2001) Biochemistry 40, 8868-8876 the terminal sialyation of a TNFR-IgG immunoadhesin was increased through a process of regalactosylation and/or resialylation using beta-1, 4-galactrosyltransferace and/or alpha, 2, 3 sialyltransferase. Increasing the terminal sialylation is believed to increase the half-life of the immunoglobulin. Antibodies, in common with most glycoproteins, are typically produced as a mixture of glycoforms. This mixture is particularly apparent when antibodies are produced in eukaryotic, particularly mammalian cells. A variety of methods have been developed to manufacture defined glycoforms, see Zhang et al, Science (2004), 303, 371; Sears et al, Science (2001), 291, 2344; Wacker et al (2002), Science 298, 1790; Davis et al (2002), Chem Rev 102, 579; Hang et al (2001), AccChem Res 34, 727. Thus the invention contemplates a plurality of therapeutic (monoclonal) antibodies (which may be of the IgGisotype, e.g. IgG1) as herein described comprising a defined number (e.g. 7 or less, for example 5 or less such as two or a single) glycoform(s) or said antibodies or antigen binding fragments thereof.

Further embodiments of the invention include therapeutic antibodies of the invention or antigen binding fragments thereof coupled to a non-proteinaceous polymer such as polyethylene glycol (PEG), polypropylene glycol or polyoxyalkylene. Conjugation of proteins to PEG is an established technique for increasing half-life of proteins, as well as reducing antigenicity and immunogenicity of proteins. The use of PEGylation with different molecular weights and styles (linear or branched) has been investigated with intact antibodies as well as Fab' fragments (see Koumenis I L et al (2000) Int J Pharmaceut 198; 83-95).

4.2 Adnectins—Compound Therapeutics

The adnectin scaffolds are based on fibronectin type III domain (e.g., the tenth module of the fibronectin type III (10

Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands. (U.S. Pat. No. 6,818,418).

These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based compounds can be used as scaffolds where the loop regions of the compound can be replaced with CDRs of the invention using standard cloning techniques. Accordingly, in some embodiments there is provided an adnectin compound that binds with c10orf99 and/or GPR15 and inhibits the interaction between ligand and receptor.

4.3 Ankyrin—Molecular Partners

This technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display. Accordingly, in some embodiments there is provided an Ankyrin compound that binds with c10orf99 and/or GPR15 and inhibits the interaction between ligand and receptor.

4.4 Maxybodies/Avimers—Avidia

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, US20040175756; US20050053973; US20050048512; and US20060008844. Accordingly, in some embodiments there is provided a Maxybody compound that binds with c10orf99 and/or GPR15 and inhibits the interaction between ligand and receptor.

4.5 Protein A—Affibody

Affibody® affinity ligands are small, simple proteins composed of a three-helix bundle based on the scaffold of one of the IgG-binding domains of Protein A. Protein A is a surface protein from the bacterium Staphylococcus aureus. This scaffold domain consists of 58 amino acids, 13 of which are randomized to generate Affibody® libraries with a large number of ligand variants (See e.g., U.S. Pat. No. 5,831,012). Affibody® compounds mimic antibodies, they have a molecular weight of 6 kDa, compared to the molecular weight of antibodies, which is 150 kDa. In spite of its small size, the binding site of Affibody® compounds is similar to that of an antibody. Accordingly, in some embodiments there is provided an Protein A-affibody compound that binds with c10orf99 and/or GPR15 and inhibits the interaction between ligand and receptor.

4.6 Anticalins—Pieris

Anticalins® are products developed by the company PierisProteoLab AG. They are derived from lipocalins, a widespread group of small and robust proteins that are usually involved in the physiological transport or storage of chemically sensitive or insoluble compounds. Several natural lipocalins occur in human tissues or body liquids.

The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain.

The set of four loops, which makes up the binding pocket, shows pronounced structural plasticity and tolerates a variety of side chains. The binding site can thus be reshaped in a proprietary process in order to recognize prescribed target compounds of different shape with high affinity and specificity.

One protein of lipocalin family, the bilin-binding protein (BBP) of PierisBrassicae has been used to develop anticalins by mutagenizing the set of four loops. One example of a patent application describing "anticalins" is PCT WO 199916873.

Accordingly, in some embodiments there is provided an anticalin compound that binds with c10orf99 and/or GPR15 and inhibits the interaction between ligand and receptor.

4.7 Affilin—Scil Proteins

Affilin™ compounds are small non-immunoglobulin proteins which are designed for specific affinities towards proteins and small compounds. New Affilin™ compounds can be very quickly selected from two libraries, each of which is based on a different human derived scaffold protein. Affilin™ compounds do not show any structural homology to immunoglobulin proteins. Scil Proteins employs two Affilin™ scaffolds, one of which is gamma crystalline, a human structural eye lens protein and the other is "ubiquitin" superfamily proteins. Both human scaffolds are very small, show high temperature stability, and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368. Accordingly, in some embodiments there is provided an Affilin compound that binds with c10orf99 and/or GPR15 and inhibits the interaction between ligand and receptor.

4.7.1—Other Therapeutic Modalities

As noted previously, other therapeutic modalities of the invention include modulators (particularly inhibitors) of GPR15 which exert their effect on their target prior to protein expression. Examples include anti-sense oligonucleotides that comprise (or consist essentially of) a sequence (a) capable of forming a stable triplex with a portion of the GPR15 gene, or (b) capable of forming a stable duplex with a portion of an mRNA transcript of the GPR15 gene under physiological conditions. Other examples include molecules that can participate in the phenomena of "RNA interference". RNA interference (RNAi) is particularly useful for specifically inhibiting the production of a particular protein.

Although not wishing to be limited by theory, Waterhouse et al. (1998) have provided a model for the mechanism by which dsRNA (duplex RNA) can be used to reduce protein production. Conveniently, the dsRNA can be produced from a single promoter in a recombinant vector or host cell, where the sense and anti-sense sequences are flanked by an unrelated sequence which enables the sense and anti-sense sequences to hybridise to form the dsRNA molecule with the unrelated sequence forming a loop structure. The design and production of suitable dsRNA molecules for the present invention is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded RNA product(s) with homology to the target gene to be inactivated.

The DNA therefore comprises both sense and antisense sequences that, when transcribed into RNA, can hybridise to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from an endogenous mammalian system that destroys both the double stranded RNA and also the homologous RNA transcript from the target mammalian gene, efficiently reducing or eliminating the activity of the target gene.

The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilise the molecule. The RNA molecule may be expressed under the control of a RNA polymerase II or RNA polymerase HI promoter. Examples of the latter include tRNA or snRNA promoters.

Preferred small interfering RNA ('siRNA") molecules comprise a nucleotide sequence that is identical to about 19-21 contiguous nucleotides of the target mRNA. Preferably, the siRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the mammal in which it is to be introduced, for example as determined by standard BLAST search.

MicroRNA regulation is a clearly specialised branch of the RNA silencing pathway that evolved towards gene regulation, diverging from conventional RNAi/PTGS.

MicroRNAs are a specific class of small RNAs that are encoded in gene-like elements organised in a characteristic inverted repeat. When transcribed, microRNA genes give rise to stem-looped precursor RNAs from which the microRNAs are subsequently processed. MicroRNAs are typically about 2 1 nucleotides in length. The released miRNAs are incorporated into RISC-like complexes containing a particular subset of Argonaute proteins that exert sequence-specific gene repression (see, for example, Millar and Waterhouse, 2005; Pasquinelli et al. 2005; Almeida and Allshire, 2005).

4.8 Production Methods

Therapeutic proteins of the invention, and particularly antibodies may be produced as a polyclonal population but are more preferably produced as a monoclonal population (that is as a substantially homogenous population of identical antibodies directed against a specific antigenic binding site). It will of course be apparent to those skilled in the art that a population implies more than one antibody entity. Antibodies of the present invention may be produced in transgenic organisms such as goats (see Pollock et al (1999), J. Immunol. Methods 231:147-157), chickens (see Morrow K J J (2000) Genet. Eng. News 20:1-55, mice (see Pollock et al) or plants (see Doran P M, (2000) Curr. Opinion Biotechnol. 11, 199-204, Ma J K-C (1998), Nat. Med. 4; 601-606, Baez J et. al, BioPharm (2000) 13: 50-54, Stoger E et al; (2000) Plant Mol. Biol. 42:583-590).

Antibodies may also be produced by chemical synthesis. However, antibodies and other therapeutic proteins of the invention are typically produced using recombinant cell culturing technology well known to those skilled in the art. A polynucleotide encoding the antibody is isolated and inserted into a replicable vector such as a plasmid for further cloning (amplification) or expression. One useful expression system is a glutamate synthetase system (such as sold by LonzaBiologies), particularly where the host cell is CHO or NSO (see below). Polynucleotide encoding the antibody is readily isolated and sequenced using conventional procedures (e.g. oligonucleotide probes). Vectors that may be used include plasmid, virus, phage, transposons, minichromosomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotide encoding the light and heavy chains may be inserted into separate vectors and transfected into the same host cell or, if desired both the heavy chain and light chain can be inserted into the same vector for transfection into the host cell.

Thus according to one aspect of the present invention there is provided a process of constructing a vector encoding the light and/or heavy chains of a therapeutic antibody or antigen binding fragment thereof of the invention, which method comprises inserting into a vector, a polynucleotide encoding either a light chain and/or heavy chain of a therapeutic antibody of the invention.

4.8.1 Signal Sequences

Antibodies of the present invention may be produced as a fusion protein with a heterologous signal sequence having a specific cleavage site at the N terminus of the mature protein. The signal sequence should be recognised and processed by the host cell. For prokaryotic host cells, the signal sequence may be an alkaline phosphatase, penicillinase, or heat stable enterotoxin Il leaders. For yeast secretion the signal sequences may be a yeast invertase leader, alpha factor leader or acid phosphatase leaders see e.g. WO90/13646. In mammalian cell systems, viral secretory leaders such as herpes simplex gD signal and a native immunoglobulin signal sequence are available. Typically the signal sequence is ligated in reading frame to DNA encoding the antibody of the invention.

4.8.2 Origin of Replication

Origin of replications are well known in the art with pBR322 suitable for most gram-negative bacteria, 2µ plasmid for most yeast and various viral origins such as SV40, polyoma, adenovirus, VSV or BPV for most mammalian cells. Generally the origin of replication component is not needed for mammalian expression vectors but the SV40 may be used since it contains the early promoter.

4.8.3 Selection Marker

Typical selection genes encode proteins that (a) confer resistance to antibiotics or other toxins e.g. ampicillin, neomycin, methotrexate or tetracycline or (b) complement auxotrophic deficiencies or supply nutrients not available in the complex media. The selection scheme may involve arresting growth of the host cell. Cells, which have been successfully transformed with the genes encoding the therapeutic antibody of the present invention, survive due to e.g. drug resistance conferred by the selection marker. Another example is the so-called DHFR selection marker wherein transformants are cultured in the presence of methotrexate. In typical embodiments, cells are cultured in the presence of increasing amounts of methotrexate to amplify the copy number of the exogenous gene of interest. CHO cells are a particularly useful cell line for the DHFR selection. A further example is the glutamate synthetase expression system (LonzaBiologies). A suitable selection gene for use in yeast is the trp1 gene, see Stinchcomb, et al. (1979) Nature 282, 38.

4.8.4 Promoters

Suitable promoters for expressing antibodies of the invention are operably linked to DNA/polynucleotide encoding the antibody. Promoters for prokaryotic hosts include phoA promoter, Beta-lactamase and lactose promoter systems, alkaline phosphatase, tryptophan and hybrid promoters such as Tac. Promoters suitable for expression in yeast cells include 3-phosphoglycerate kinase or other glycolytic enzymes e.g. enolase, glyceraldehyde 3 phosphate dehydrogenase, hexokinase, pyruvate decarboxylase, phosphofructokinase, glucose 6 phosphate isomerase, 3-phosphoglyceratemutase and glucokinase. Inducible yeast promoters include alcohol dehydrogenase 2, isocytochrome C, acid phosphatase, metallothionein and enzymes responsible for nitrogen metabolism or maltose/galactose utilization.

Promoters for expression in mammalian cell systems include viral promoters such as polyoma, fowlpox and adenoviruses (e.g. adenovirus 2), bovine papilloma virus, avian sarcoma virus, cytomegalovirus (in particular the immediate early gene promoter), retrovirus, hepatitis B virus, actin, rous sarcoma virus (RSV) promoter and the early or late Simian virus 40. Of course the choice of promoter is based upon suitable compatibility with the host cell used for expression.

4.8.5 Enhancer Element

Where appropriate, e.g. for expression in higher eukaroytics, an enhancer element operably linked to the promoter element in a vector may be used. Suitable mammalian enhancer sequences include enhancer elements from globin, elastase, albumin, fetoprotein and insulin. Alternatively, one may use an enhancer element from a eukaroytic cell virus such as SV40 enhancer (at bp 100-270), cytomegalovirus early promoter enhancer, polyma enhancer, baculoviral enhancer or murine lgG2a locus (see WO04/009823). The enhancer is preferably located on the vector at a site upstream to the promoter.

4.8.6 Host Cells

Suitable host cells for cloning or expressing vectors encoding antibodies of the invention are prokaroytic, yeast or higher eukaryotic cells. Suitable prokaryotic cells include eubacteria e.g. enterobacteriaceae such as *Escherichia* e.g. *E. Coli* (for example ATCC 31, 446; 31, 537; 27,325), *Enterobacter, Erwinia, Klebsiella Proteus, Salmonella* e.g. *Salmonella typhimurium, Serratia* e.g. *Serratiamarcescans* and *Shigella* as well as *Bacilli* such as *B. subtilis* and *B. licheniformis* (see DD 266 710), *Pseudomonas* such as *P. aeruginosa* and *Streptomyces*. Of the yeast host cells, *Saccharomyces cerevisiae, schizosaccharomycespombe, Kluyveromyces* (e.g. ATCC 16,045; 12,424; 24178; 56,500), *yarrowia* (EP402, 226), *Pichia Pastoris* (EP183, 070, see also Peng, et al. (2004) J. Biotechnol. 108 (185-192), *Candida, Thchodermareesia* (EP244, 234J, *Penicillin, Tolypocladium* and *Aspergillus* hosts such as *A. nidulans* and *A. niger* are also contemplated.

Although Prokaryotic and yeast host cells are specifically contemplated by the invention, preferably however, host cells of the present invention are higher eukaryotic cells. Suitable higher eukaryotic host cells include mammalian cells such as COS-1 (ATCC No. CRL 1650) COS-7 (ATCC CRL 1651), human embryonic kidney line 293, baby hamster kidney cells (BHK) (ATCC CRL. 1632), BHK570 (ATCC NO: CRL 10314), 293 (ATCC NO. CRL 1573), Chinese hamster ovary cells CHO (e.g. CHO-K1, ATCC NO: CCL 61, DHFR-CHO cell line such as DG44 (see Urlaub, et al. (1986) Somatic Cell Mol. Genet. 12, 555-556)), particularly those CHO cell lines adapted for suspension culture, mouse Sertoli cells, monkey kidney cells, African green monkey kidney cells (ATCC CRL-1587), HELA cells, canine kidney cells (ATCC CCL 34), human lung cells (ATCC CCL 75), Hep G2 and myeloma or lymphoma cells e.g. NSO (see U.S. Pat. No. 5,807,715), Sp2/0, YO. Thus in one embodiment of the invention there is provided a stably transformed host cell comprising a vector encoding a heavy chain and/or light chain of the therapeutic antibody or antigen binding fragment thereof as herein described. Preferably such host cells comprise a first vector encoding the light chain and a second vector encoding said heavy chain.

4.6.1 Bacterial Fermentation

Bacterial systems may be used for the expression of non-immunoglobulin therapeutic proteins described above. Bacterial systems are also particularly suited for the expression of antibody fragments. Such fragments are localised intracellular or within the periplasma. Insoluble periplasmic proteins can be extracted and refolded to form active proteins according to methods known to those skilled in the art, see Sanchez et al (1999) J. Biotechnol. 72, 13-20 and Cu pit P M et al (1999) Lett. Appl. Microbiol. 29, 273-277.

4.8.7 Cell Culturing Methods

Host cells transformed with vectors encoding the therapeutic antibodies of the invention or antigen binding fragments thereof may be cultured by any method known to those skilled in the art. Host cells may be cultured in spinner flasks, roller bottles or hollow fibre systems but it is preferred for large scale production that stirred tank reactors are used particularly for suspension cultures. Preferably the stirred tankers are adapted for aeration using e.g. spargers, baffles or low shear impellers. For bubble columns and airlift reactors direct aeration with air or oxygen bubbles may be used. Where the host cells are cultured in a serum free culture media it is preferred that the media is supplemented with a cell protective agent such as pluronic F-68 to help prevent cell damage as a result of the aeration process.

Depending on the host cell characteristics, either microcarriers may be used as growth substrates for anchorage dependent cell lines or the cells may be adapted to suspension culture (which is typical). The culturing of host cells, particularly invertebrate host cells may utilise a variety of operational modes such as fed-batch, repeated batch processing (see Drapeau, et al. (1994) Cytotechnology 15: 103-109), extended batch process or perfusion culture. Although recombinantly transformed mammalian host cells may be cultured in serum-containing media such as fetal calf serum (FCS), it is preferred that such host cells are cultured in synthetic serum-free media such as disclosed in Keen, et al. (1995) Cytotechnology 17:153-163, or commercially available media such as ProCHO-CDM or UltraCHO™ (Cambrex N.J., USA), supplemented where necessary with an energy source such as glucose and synthetic growth factors such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see e.g. Scharfenberg K et al (1995) in Animal Cell technology: Developments towards the 21st century (Beuvery E. G. et al eds), pp 619-623, Kluwer Academic publishers).

Antibodies or other therapeutic proteins of the invention secreted into the media may be recovered and purified using a variety of techniques to provide a degree of purification suitable for the intended use. For example the use of therapeutic antibodies of the invention for the treatment of human subjects typically mandates at least 95% purity, more typically 98% or 99% or greater purity (compared to the crude culture medium). In the first instance, cell debris from the culture media is typically removed using centrifugation followed by a clarification step of the supernatant using e.g. microfiltration, ultrafiltration and/or depth filtration.

A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429,746) are available. In one embodiment, the antibodies of the invention, following various clarification steps, are captured using Protein A or G affinity chromatography followed by further chromatography steps such as ion exchange and/or HA chromatography, anion or cation exchange, size exclusion chromatography and ammonium sulphate precipitation. Typically, various virus removal steps are also employed (e.g. nanofiltration using e.g. a DV-20 filter). Following these various steps, a purified (preferably monoclonal) preparation comprising at least 75 mg/ml or greater e.g. 100 mg/ml or greater of the antibody of the invention or antigen binding fragment thereof is provided and therefore forms an embodiment of the invention. Suitably such preparations are substantially free of aggregated forms of antibodies of the invention.

4.9—Screening Methods

In other embodiments there is provided a method of/for identifying modulators of the interaction between c10orf99 and GPR15. Such methods generally comprise bringing into contact c10orf99 and GPR15 in the presence of a candidate compound and observing a modulation (such as inhibition) of the interaction between either or both of the ligands c10orf99 and GPR15 compared to the same experiments in absence of the candidate compound. Candidate compounds that exhibit inhibition characteristics may be further structurally modified to improve $IC_{50}$ against its target entity and/or improve toxicity profile prior to formulation and administering to a human subject in clinical need thereof.

4.10 Pharmaceutical Compositions

The invention provides pharmaceutical compositions comprising the therapeutic protein or low molecular weight chemical entity formulated together with a pharmaceutically acceptable carrier. The compositions can additionally contain other therapeutic agents that are suitable for treating or preventing a human disease or disorder noted below. Pharmaceutically carriers enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound (particularly low molecular weight chemical entities) may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Typically, a therapeutically effective dose or efficacious dose of the modulator of NRG1 (e.g. NRG1β1) such as a NRG1β1 antibody described herein is employed in the pharmaceutical compositions of the invention. They are typically formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular subject, composition, and mode of administration, without being toxic to the subject. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject being treated, and like factors.

A physician can start doses of the antibodies of the invention employed in the pharmaceutical composition at levels lower than that required to achieve the desired therapeutic effect and gradually increase the dosage until the desired effect is achieved. In general, effective doses of the compositions of the present invention, for the treatment of an allergic inflammatory disorder described herein vary depending upon many different factors, including means of administration, target site, physiological state of the subject, whether the subject is human or an animal, other medications administered, and whether treatment is prophylactic or therapeutic. Treatment dosages need to be titrated to optimize safety and efficacy. For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months.

Antibody and other protein therapeutics are usually administered on multiple occasions. Intervals between single dosages can be weekly, monthly or yearly. Intervals can also be irregular as indicated by measuring blood levels of therapeutic protein in the subject. In some methods, dosage is adjusted to achieve a plasma antibody concentration of 1-1000 μg/ml and in some methods 25-300 μg/ml. Alternatively, antibody or other protein therapeutics can be administered as a sustained release formulation, in which case less frequent administration is required. Dosage and frequency vary depending on the half-life of the antibody or other protein therapeutic in the subject.

In general, humanized antibodies show longer half-life than that of chimaeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

Thus the invention concerns a pharmaceutical composition comprising a modulator of the interaction between c10orf99 and GPR15 together with a pharmaceutically acceptable carrier or diluent. Typically such modulators are inhibitors as described hereinbefore.

4.11 Clinical Uses

Pharmaceutical compositions of the invention comprise modulators, particularly inhibitors of the interaction between c10orf99 and GPR15, may be used in diseases or disorders responsive to the modulation of this interaction. Examples of such diseases include HIV infection and associated pathologies such as enteropathy-like malabsorption and increased paracellular permeability; psoriasis, dermatitis, and other skin disorders such as sarcoidosis and subcorneal pustular dermatosis (also known as Sneddon-Wilkinson disease); colon cancer; uveitis, asthma, chronic obstructive pulmonary disease (COPD); idiopathic pulmonary fibrosis (IPF); diseases with alteration of the epithelial function/structure (e.g., wound healing, skin inflammation, mucositis, inflammatory bowel disease (IBD), lung diseases, rheumatoid arthritis and other autoimmune diseases); lipid disorders; Crohn's disease and colitis; metabolic conditions; and mild to moderate lymphoid atrophy or hypoplasia and other immune conditions.

The methods of treatment of the invention are based, among other things, on in vivo observations made with animals overexpressing GPR15L or lacking GPR15 or GPR15L, and with various cell lines expressing GPR15 and/or GPR15L.

For example, lymph nodes from GPR15L KO (i.e., c10orf99 knockout) animals are smaller than those obtained from wild type animals, observations of which are consistent with the mild to moderate lymphoid atrophy or hypoplasia in GPR15L KO animals. The number of high endothelial venules observed in microscopic sections appear to be fewer in knockout animals.

Figure 7A:
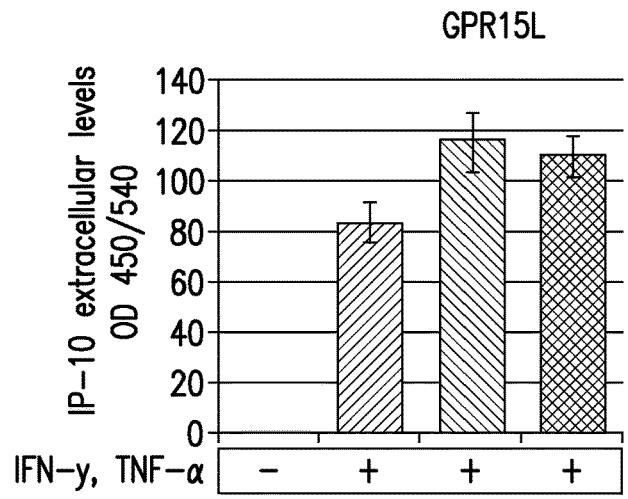
FIGS. 7A and 7B: A graphic showing that GPR15L induces IP-10 (interferon gamma-induced protein 10, also known as C—X—C motif chemokine 10 (CXCL10)) release from human neonatal dermal fibroblasts, and that GPR15L overexpression in 421G15 mouse line induces an increase in IP-10 levels in mouse sera. The two columns on the right of the graphic show GPRL-expression dermal fibroblasts stimulated by TNF alpha (the column second from the right) and INF gamma (the rightmost column).
Figure 7B:
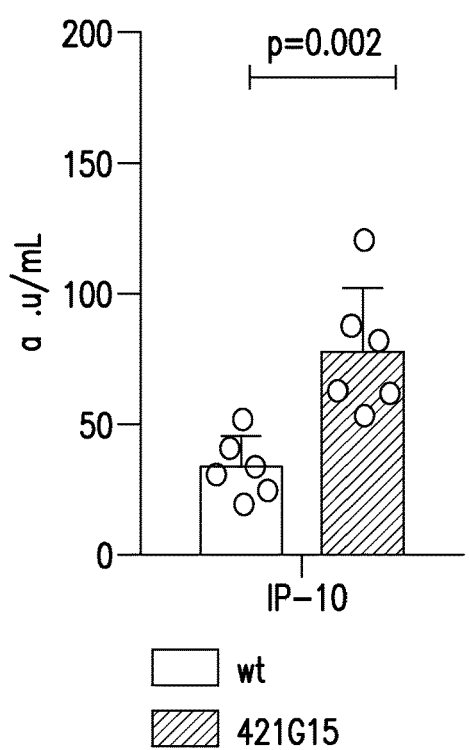

GPR15L action is also mediated by a GPR15-independent mechanism in human neonatal dermal fibroblasts. For instance, as depicted in FIG. 7, GPR15-independent c10orf99 induces IP-10-release in human neonatal dermal fibroblasts. Interferon gamma-induced protein 10 (IP-10), also known as C—X—C motif chemokine 10 (CXCL10), is secreted by monocytes, endothelial cells, and fibroblasts in response to IFN-γ. CXCL10 binds to the cell surface chemokine receptor CXCR3 and is implicated in such processes as chemoattraction for monocytes/macrophages, T cells, NK cells, and dendritic cells, promotion of T cell adhesion to endothelial cells, antitumor activity, and inhibition of bone marrow colony formation and angiogenesis.

Analysis of the blood of GPR15 knockout mice revealed a decrease in the relative number of CD3+CD4−CD8− and CD3+CD4−CD8+ in female animals (−36.1%; p=0.005 and −11.7%; p=0.015 respectively). In male animals a relative reduction in CD3+CD4−CD8− was also observed (−28.6%; p=0.05).

In female GPR15KO animals, a 19.7% increase in serum IgG2a (p=0.049), 181.5% increase in IgG2b (p=0.004), 141.3% in IgG3 (p=0.002) and 125.9.0% increase in IgM (p=0.002) was observed compared to controls. IgM/IgGisotype ratios were next examined and a 101% increase in the IgM/IgG2a ratio (p=0.006) in female animals was found.

Furthermore, alterations in lymphoid morphology and in peripheral lymphocyte subsets seen in GPR15L transgenic (i.e., high expressing) mice suggest on-going immune activation. The increased size and number of germinal centers in the spleen and the apparent lymphoid hyperplasia in the tracheal bronchiole lymph nodes supports a generalized immune activation.

In view of the above observations, agonism, allosteric potentiators, LMW agonists, antagonists of the GRP15: GRP15L relationship, e g, inhibitory antibodies, would be preferred therapeutics for autoimmune diseases or inflammatory conditions. Furthermore, the deorphaning discovery of the present invention in particular suggests that inhibitory antibodies against GPR15 would be preferred therapeutics for autoimmune diseases or inflammatory conditions.

GPR15L over- or aberrant-expression was observed to induce a body weight defect, mainly due to decreased white adipose tissue (WAT) deposits. In addition, histological evaluation of tissue section slides revealed that brown adipose tissue (BAT) structure (and possibly function) was maintained in 1 year old transgenic mice, compared to wild-type control mice. This last observation suggests GPR15L plays a role in regulating BAT homeostasis and function possibly by directly affecting adipocytes differentiation programs or by recruitment of (anti-inflammatory) immune cells. An increase in BAT functionality—increased thermogenesis—can explain the decrease in WAT.

For this reason, agonists of the GRP15:GRP15L relationship, e.g., agonist antibodies, peptide mimetics, would be preferred therapeutics for metabolic conditions requiring weight loss or appetite diminution. Furthermore, the deorphaning discovery of the present invention in particular suggests that administering GPR15L, and/or agonizing agents thereto, would be preferred therapeutics for metabolic conditions requiring weight loss or appetite diminution.

GPR15 is known to be expressed in human CD4(+) T lymphocytes and activated rhesus macaque peripheral blood mononuclear cells, and in regulatory T cells (Tregs). Our data confirm that GPR15 is expressed in regulatory T cells (Tregs). Recently GPR15 was claimed as involved in Treg homing toward the lamina propria of the large intestine, a tissue where the GPR15 ligand ("GPR15L") is known to be highly expressed. Lack of GPR15 results in a severe body weight loss with increased inflammation and tissue damage in the Citrobacterrodentium infection-induced Inflammatory Bowel Disease (IBD) mouse model (Kim et al. (2013) Science 340(6139): 1456-9). In this context, agonistic modulation of the GPR15-mediated Treg homing might be relevant in colitis diseases.

By contrast, GPR15L is expressed in some colon cancer cells (internal data). In this context antagonistic modulation of the GPR15-mediated Treg homing could trigger an increased immune response against tumours.

In SW48 cells (ATCC CCL-231 cell line, human colon cancer Dukes' type C, grade IV, colorectal adenocarcinoma) we detected GPR15 protein by immuno-cyto chemistry. On those cells GPR15L induces a dose response dependent increase in intracellular calcium levels after priming, as well as a pertussis toxin sensitive decrease in forskolin-induced cAMP elevation suggesting a G-alphai coupling as described for chemokine receptors.

Figure 6A:
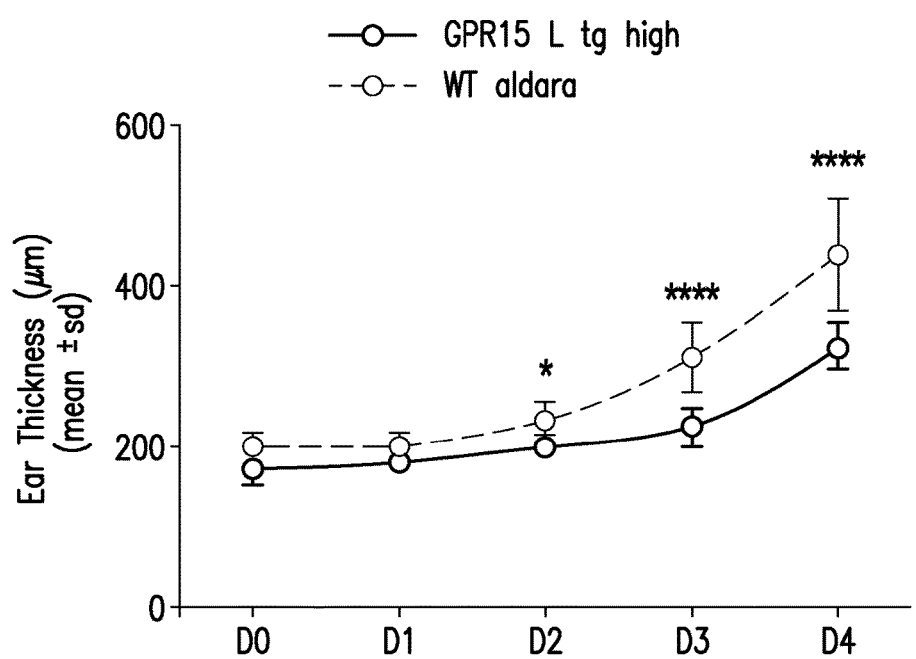
FIGS. 6A and 6B: A graphic showing that GPR15L over-expression reduces skin inflammation and remodelling after an imiquimod challenge. As depicted in 6A, ear thickness of the GPR15L expressing mice is reduced at day 4 of the imquimod challenge when compared to wild-type mice. In 6B, quantification of some inflammation markers by real time PCR at day 4 of the imiquimod challenge reveals changes such as a decrease in psoriasin (S100A7) in the GPR15L transgenic mice.
Figure 6B:
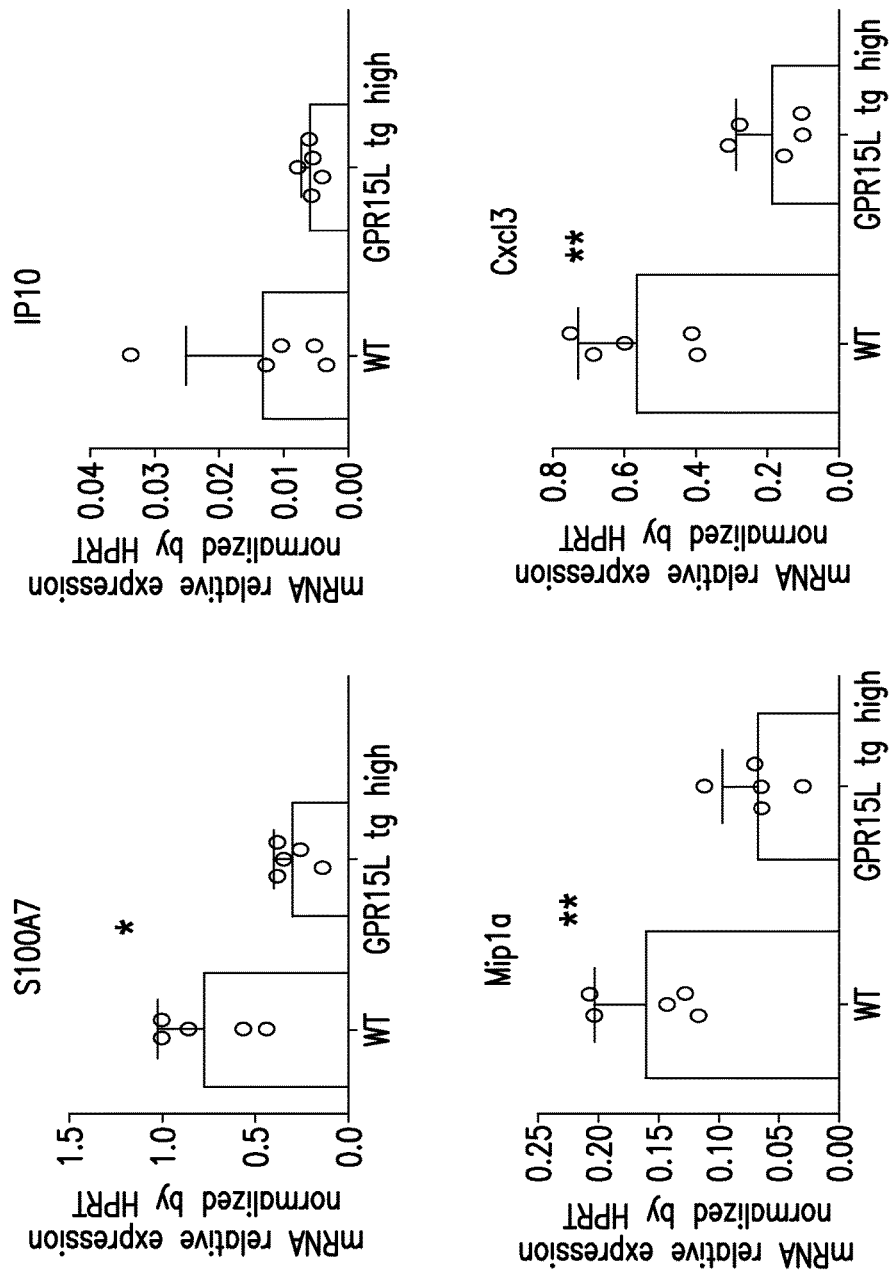

As described below and seen at least in FIGS. 6A and 6B, GPR15L over-expression reduces skin inflammation. Furthermore, increased expression of the GPR15L in the imiquimod-induced psoriasis-like skin inflammation mouse model was observed, with a maximum at D2-3 of the challenge. When tested, GPR15L Tg$^{high}$ mice displayed a decrease in ear thickness and decreased levels of inflammation markers (PCR) at day 4 of the challenge. In view of the above observations, agonists of the GPR15: GPR15L relationship, e.g., agonist entity, would be preferred therapeutics for psoriasis, dermatitis, and other skin disorders such as sarcoidosis and subcorneal pustular dermatosis (also known as Sneddon-Wilkinson disease); and diseases with alteration of the epithelial function/structure. Furthermore, the deorphaning discovery of the present invention in particular suggests that activating GPR15, and/or agonizing agents thereto, would be preferred therapeutics for said skin conditions.

5. Examples

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

5.1 GPR15 Recombinant Cell Lines

Human GPR15 gene was cloned using RT-PCR from genomic DNA and corresponds to Genbank accession number U34806.1. Human GPR15 was inserted into the pEFIN3 vector (a Euroscreen proprietary vector) at the EcoR1 and BamH1 sites in the multiple cloning sites. Mouse GPR15 was cloned using RT-PCR from mouse genomic DNA and corresponds to GenBank accession number Q0VDU3. Mouse GPR15 was inserted into the pEFIN5 vector (Euroscreen proprietary vector) at the EcoR1 and Xba1 sites in the multiple cloning sites.

Plasmids encoding human and mouse GPR15 were stably transfected in CHO, 1321 N1 and HEK293 cells expressing the apoaequorin (CHO-Aeq, 1321-N1-Aeq and HEK-Aeq). GPR15 mRNA sequence integrities were checked using RT-PCR at T0 and T30 culture times in CHO cells.

5.2 Human and Mouse GPR15 Monoclonal Antibody

An N-terminus-tagged-version of human and mouse GPR15 monoclonal antibody were used to verify stable plasma membrane expression of GPR15 in recombinant CHO and 1321N1 cells (a human brain astrocytoma cell line) using flow cytometry. A monoclonal antibody validated for flow cytometry is available from R&D systems (Catalogue #: MAB3654)

5.3 Primary Screening 5.3.1 Specific Activation of GPR15 with Fractions from Porcine Colon Extract An hGPR15 CHO-G$_{\alpha16}$Aeq cell line was used for the Aequorin screening of Euroscreen proprietary libraries of natural ligands and tissue extracts collection. Specific activation of GPR15 over more than 20 other orphan GPCRs was identified in fractions from a colon aqueous extract.

5.3.2 Peptidic Nature of the Identified GPR15 Activity

As depicted in FIG. 1, the peptidic structure of the GPR15 ligand was revealed as treatment of the GPR15 active colon fraction (F28) by proteinase K failed to induce GPR15 activation.

5.4 Results

5.4.1 Purification of GPR15 Ligand from and Aqueous Porcine Colon Extract Extraction and Purification Procedures Purification of GPR15 ligand was initiated using porcine colon, as a non limiting source of tissue. 3.8 kilograms of porcine colon were extracted and fractionated following 5 steps of liquid chromatography to obtain pure fractions that potently activated GPR15 receptor.
Experimental Procedure:

Small pieces of frozen porcine colon (~300 g) were added to boiling water (2.5 liters) for 5 minutes. After homogenisation in a blender and acidification with acetic acid to 1 M, the homogenate was centrifuged (30 min, 12,000 g, 4° C.). The supernatant was then extracted with dichloromethane (5:1 V/V) twice. The aqueous phase was again centrifuged (15 min, 12,000 g, 4° C.) and filtered through 0.45 μm filters. The filtrate was then loaded on a C18 column (Waters Delta-Pak, 40×300 mm, 15 μm, 300 Å) conditioned with 5% MeCN+0.1% TFA at 100 mL/min. Elution was performed with 80% MeCN+0.1% TFA. The eluate was partially concentrated under reduced pressure and diluted 3 times with 0.1% TFA in water.

The first separation was conducted a C18 column (Waters DeltaPak, 25×300 mm, 15 μm, 300 Å) equilibrated with 5% MeCN+0.1% TFA at 40 mL/min. A linear 5-95% MeCN+ 0.1% TFA gradient at 1%/min was applied.

Each collected fraction (40 mL) was tested for ability to activate GPR15 using aequorin assay. Active fractions at around 30% MeCN+0.1% TFA were subjected to a second purification step on a WCX column (Poly LC PolyCat A, 9.4×200 mm, 5 μm, 300 Å) equilibrated with NH4OAc 10 mM at 3 mL/min (10 times). 20 mL of active fraction mixed with 1 mL of 1M NH4OAc were pumped onto the column and a linear gradient to 1M NH4OAc at 10%/min was subjected. Two zones of GPR15 activity were detected.

Purification was continued with the second fraction corresponding to the most charged peptide.

For the third step of purification, an aliquot of each of the pooled active fractions (8 mL) was mixed with 8 mL of 10 mM HFBA in water and chromatographed on a C18 column (ACE, 7.75×250, 5 μm, 300 Å) using a 15-65% linear gradient at 0.5%/min. of 10 mM HFBA in water to 10 mM HFBA in MeCN at 3 mL/min.

For the fourth step of purification, active fractions from the 3$^{rd}$ step (2 mL) mixed with 5 mL of 10 mM phosphate buffer pH 3 were then pumped on a C18 column (Vydac, 250×4.6, 5 μm, 300 Å) equilibrated with 5% MeCN in 10 mM phosphate buffer pH3. A linear gradient at 0.3%/min, from 15 to 40% MeCN in 10 mM phosphate buffer pH3, at 1 mL/min was used for elution.

Active fractions from the 4$^{th}$ step were subjected to a 5$^{th}$ step of purification. Pooled active fractions (1 mL) were mixed with 1 mL 0.1% HCOOH in water and injected on a C8 column (Vydac, 250×2.1 mm, 5 μm, 300 Å) equilibrated with 5% MeCN+0.1% HCOOH. A 1%/min 5-40% MeCN+ 0.1% HCOOH linear gradient at 300 μL/min was selected for peptide elution.

At this stage the active fractions appeared associated with a single peak and the material was subjected to structural analysis.

5.4.2 Identification of GPR15 Ligand from Aqueous Porcine Extract MS Analysis Using matrix-assisted laser desorption/ionization mass spectrometry (MALDI-MS) in linear mode (2 μL+1 μL sinapinic acid (saturated solution 1:1 H$_2$O/CH$_3$CN+0.1% TFA), a candidate at m/z ~6500 was identified that corresponded to GPR15 activity seen in analysed fractions. Initial N-terminal Edman sequencing (20 μL on PVDF membrane) revealed the RRHPRNPAKXGkIXi (SEQ ID NO:1) sequence while de novo sequencing performed on the tryptic digest after nanoLC-MS$^E$ revealed a peptide at 1659.96 m/z corresponding to the QKPQLWVVPGALPQV (SEQ ID NO: 2) sequence and a peptide at 1095.61 m/z sequenced as LPGPDLMPQK (SEQ ID NO: 3).

The *Sus scrofa* (pig) peptide candidate identified from MS analysis and database searching is as follows:

```
                                         (SEQ ID NO: 4)
RRHPRNPAKP GKIRICCPRL PGPDLMPQKG HHMRICRPCK
FKQKPQLWVV PGALPQV
```

Amino acids 1-15 represent sequence identified by Edman sequencing Amino acids 20-29 and 43-57 are tryptic peptides sequenced by MS$^E$.

The structure of human c10orf99 encoding peptide is as follows (molecular weight of 6518):

```
                                         (SEQ ID NO: 5)
MRLLVLSSLL CILLLCFSIF STEGKRRPAK AWSGRRTRLC
CHRVPSPNST NLKGHHVRLC KPCKLEPEPR LWVVPGALPQ
V
```

The predicted signal peptide is residues 1-24.

These data identified the porcine ortholog of human c10orf99 as the candidate ligand for GPR15 (SEQ ID NO:4). The human ortholog of this polypeptide is encoded by the human c10orf99 gene and maps on chromosome 10 at 10q23.1. The protein is referenced as Genbank accession number: NP_997256.1 (SEQ ID NO: 5).

5.4.3 Identification of the GPR15 Natural Ligand: Activation of hGPR15 and mGPR15 by c10orf99

Figure 2:
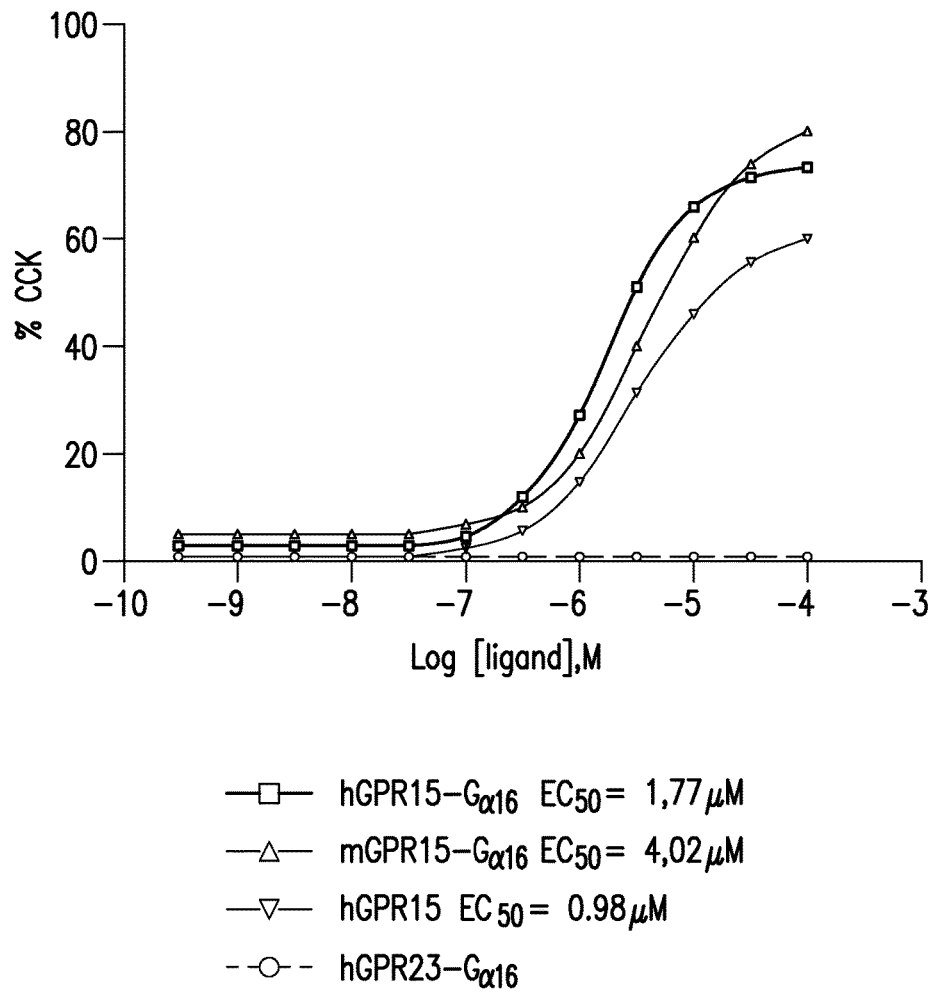
FIG. 2: A graphical depiction of the activation of human and mouse GPR15 stably expressed in CHO-Aequorin (with or without $G_{\alpha 16}$) cells by QKPQLWVVPGALPQV peptide (SEQ ID NO: 2) (i.e., the putative tryptic C-term fragment (43-57) of the porcine c10orf99 peptide). Luminescence signal obtained in response to GPR15L in the cells expressing the human (hGPR15) or murine (mGPR15) receptor is represented as a percentage of the cholecystokinin response. Cells expressing the non-related hGPR23 receptor failed in responding to GPR15L.

QKPQLWVVPGALPQV peptide (SEQ ID NO: 2), corresponding to a putative tryptic C-term fragment (43-57) of the porcine peptide, was first synthesised for GPR15 evaluation. This peptide was tested for human and mouse GPR15 activation in an Aequorin assay (as can be seen in FIG. 2) and revealed specific activation of GPR15 over GPR23 with an EC$_{50}$ of ~2 μM. This peptide (43-57; SEQ ID NO: 2) was also able to activate hGPR15 CHO cell line with the same affinity indicating that GPR15 couples to calcium via Gq or Gi through βγ. This activation by the 43-57 peptide (SEQ ID NO: 2) suggest that the identified candidate is the natural ligand for GPR 15.

CHO Production

To confirm the GPR15 natural ligand and its affinity, a cDNA encoding the human c10orf99 sequence (SEQ ID NO: 5) was constructed, transferred into pEFIN5 vector and transfected in CHO cells to obtain a pool of cells expressing the polypeptide of SEQ ID NO: 5.

For recombinant c10orf99 production, cells were grown to 70% confluence and further incubated with serum-free DMEM-F12, after 24 hours, a DMSO/Butyrate mixture (1%/7.5 mM respectively) was added to the medium which was collected after 3 days. The recombinant protein was purified with 3 HPLC purification steps: C18 25 mm eluted with MeCN+0.1% TFA at 1%/min, C18 7.75 mm eluted with MeCN+10 mM HFBA at 0.5% min and C8 4.6 mm eluted with MeCN+0.1% TFA at 0.5%/min. Concentration was determined using a microBCA assay with BSA as calibrator.

In Vitro Production

Additionally, a cDNA coding for the mature c10orf99 polypeptide less the first methionine residue was transferred into vector and expressed using agglutinin wheat germ extract (In-Vitro (IV) production). After 2 HPLC purification steps (C18 7.75 mm eluted with MeCN+10 mM HFBA at 0.5% min and C8 4.6 mm eluted with MeCN+0.1% TFA at 0.5%/min), pure peptide was obtained and quantified using a microBCA assay with BSA as calibrator.

Figure 3:
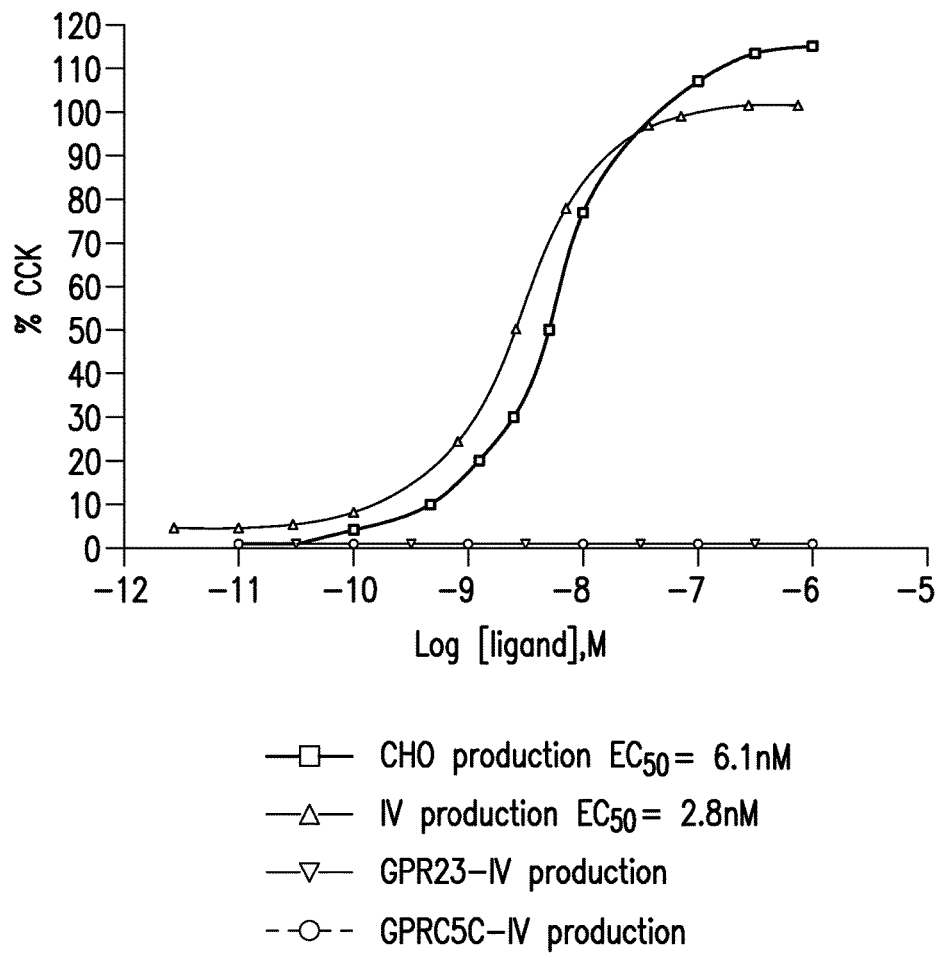
FIG. 3: Demonstration of the selectivity of c10orf99 for GPR15 over other GPCR family members. Human GPR15 (hGPR15) stably expressed in CHO-Aeq cells is specifically activated by c10orf99 peptide as shown by an aequorin assay. Efficacy of the ligand purified from recombinant CHO cells (CHO production) or from In Vitro translation preparation (IV preparation) is comparable on the human GPR15 receptor and failed to induce any calcium signal on the human GPR23 or GPRC5C.

Both peptides (i.e., those produced via CHO production and in vitro production in the agglutinin wheat germ extract system) were tested for GPR15 activation using Aequorin dose response curves. The data demonstrates that c10orf99 peptides activate specifically and selectively GPR15 compared to CHO-Aeq $G_{\alpha16}$ expressing unrelated GPCRs such as orphan GPR23 and GPRC5C. This selectivity is demonstrated in FIG. 3.

Figure 4:
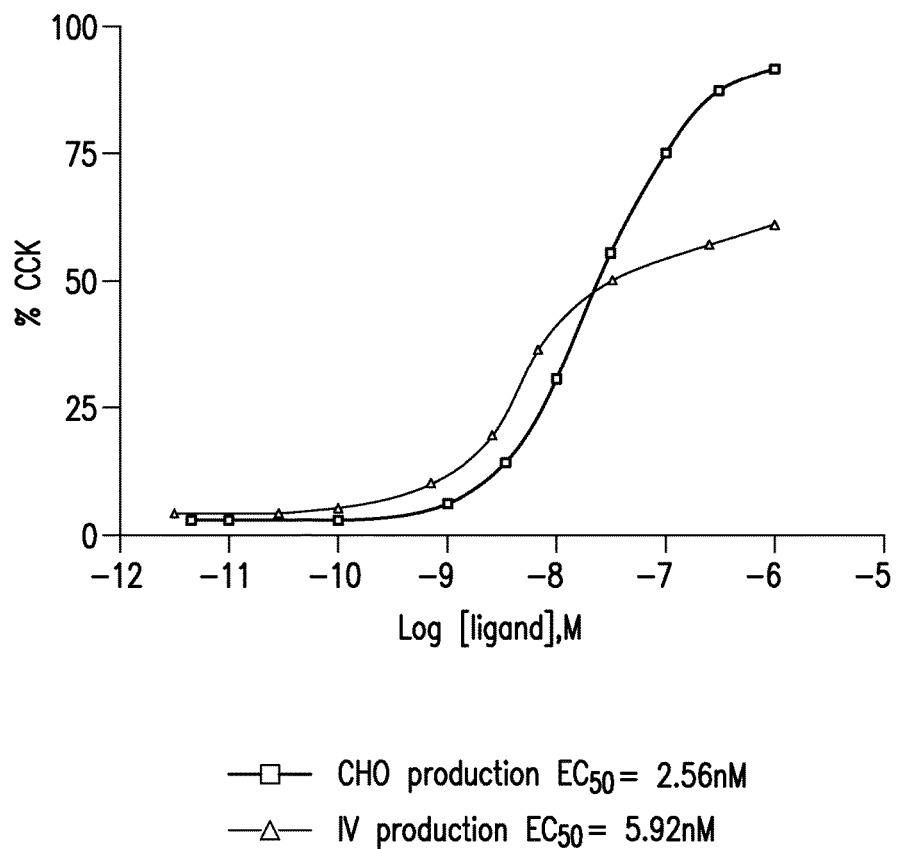
FIG. 4: A graphical depiction of the activation of mouse GPR15 (mGPR15) stably expressed in CHO-Aeq cells (aequorin assay). Efficacy of the ligand purified from recombinant CHO cells (CHO production) or from In Vitro translation preparation (IV preparation) is comparable on murine GPR15 receptor.
Figure 5A:
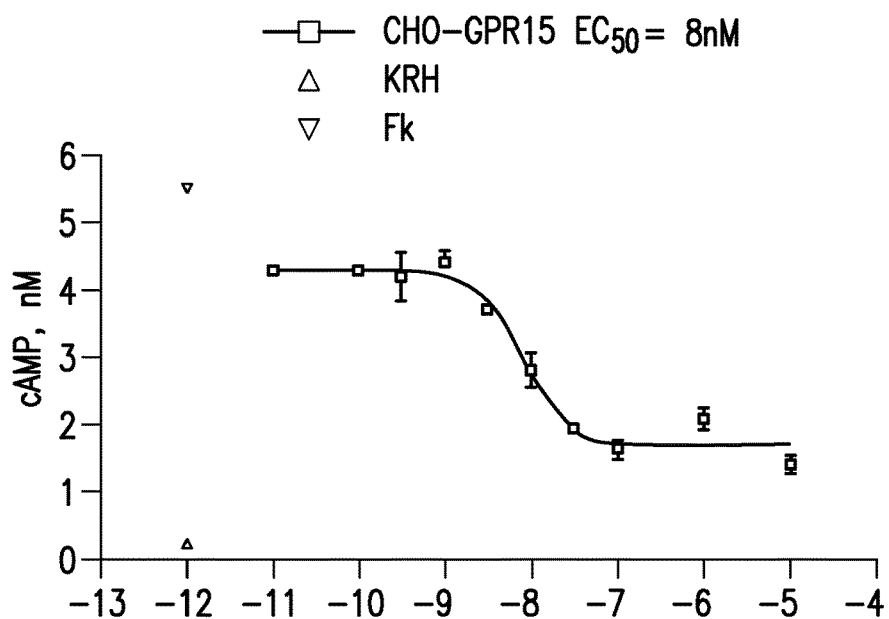
FIGS. 5A and 5B: A graphical depiction of the activation of human GPR15 (hGPR15) stably expressed in CHO and HEK cells with c10orf99 1-57 (cAMP HTRF assay).
Figure 5B:
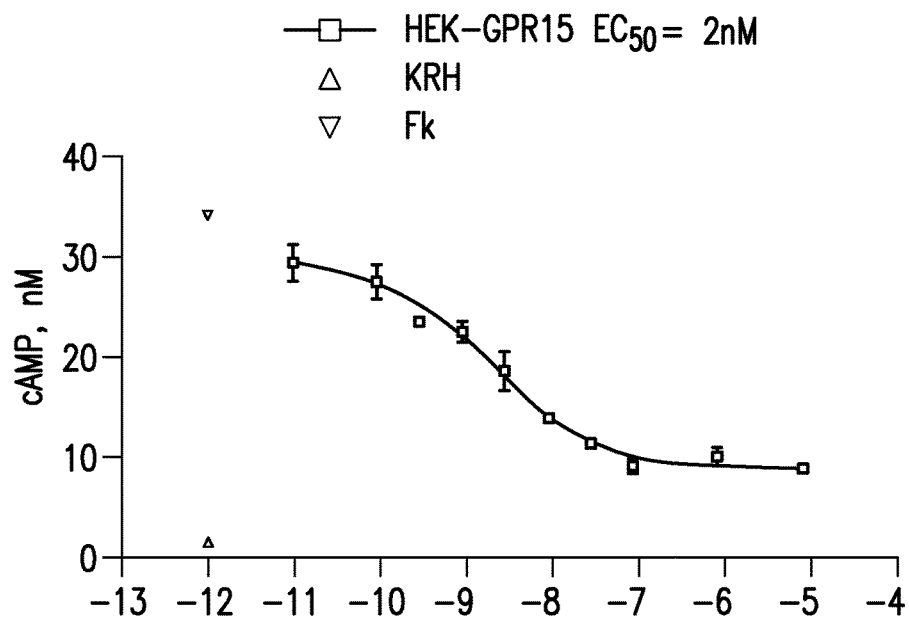

Activation of mouse GPR15 receptor was observed with both the CHO and IV produced sources of polypeptide, as seen in FIG. 4. Finally, activation of hGPR15 in stably transfected in HEK-Aeq $G_{\alpha16}$ cells was confirmed, as seen in FIG. 5.

As seen in FIG. 6, the synthetic peptide KRRPAKAWSGRRTRLCCHRVPSPNSTNLKGHHVRL-CKPCK LEPEPRLWVVPGALPQV (SEQ ID NO: 6) was evaluated on CHO and HEK cells stably expressing hGPR15 for the ability to couple through Gi using a HTRF assay.

5.5 Regulation of c10orf99 in Psoriasis

Transcriptome analysis of skin from control (58) and psoriasis subjects (64) shows that c10orf99 is the most upregulated transcript (40 fold increase) in psoriatic skin. (Gudjonsson et al. J. Inv. Derm. 2009; Zhou et al. Physiol. Genom. 2003). As seen in FIG. 7, subjects treated for psoriasis with secukinumab (AIN457), a fully human monoclonal antibody that selectively binds to and neutralizes IL-17A, have a significant decrease in c10orf99 mRNA after 4 weeks and 58% reduction in the Psoriasis Area and Severity Index (PAST) (Hueber et al. Sci. Transl. Med. Vol. 2(52):52ra72.)

As seen in FIGS. 8A and 8B, GPR15L over-expression reduces skin inflammation and remodelling after an imiquimod challenge. GPR15L expression results in a significant modulation of the transcriptome such as a decrease of KLK6, S100A8, S100A9, IL-17a, Lce3f, CXCL2, RPTN, SPRR2 mRNA or an increase in IL-10, CCL-20, RORγt RNA at D4 of the imiquimod challenge. Briefly, five wild type mice and five GPR15 L knockout mice were treated every day for 4 days by application of imiquimod (Aldara-creme 5%, 25 mg bag for 5 mice) under Isofluranesthesia on both ear. Body weight and ear thickness were evaluated daily. At day four, the mice were sacrificed and tissues collected for further characterization by histology, quantitative PCR or cytokine measurements.

Such data suggests that agonists of the GPR15:GPR15L interaction could be useful therapeutics for conditions associated with inflammation and/or autoimmunity, including but not limited to diseases with alteration of the epithelial function/structure (e.g., wound healing, skin inflammation, mucositis, inflammatory bowel disease (IBD), lung diseases, rheumatoid arthritis and other autoimmune diseases); Crohn's disease and colitis; and psoriasis, dermatitis, and other skin disorders such as sarcoidosis and subcorneal pustular dermatosis (also known as Sneddon-Wilkinson disease).

The invention claimed is:

1. A method of identifying a modulator of the binding between C10orf99 and GPR15 which method comprises;
   (a) providing a candidate modulator;
   (b) incubating the modulator of step (a) with C10orf99 having the amino acid sequence of SEQ ID NO:2 or SEQ ID NO:6 and GPR15 having the amino acid sequence of SEQ ID NO: 9, SEQ ID NO: 10 or SEQ ID NO: 11;
   (c) determining whether the binding between C10orf99 with GPR15 is modulated in the presence of said candidate modulator compared to the binding between C10orf99 with GPR15 in the absence of said candidate modulator.

2. A method of identifying an agent that modulates the binding between c10orf99 and GPR15, said method comprising:
   (a) contacting GPR15 having the amino acid sequence of SEQ ID NO: 9, SEQ ID NO: 10 or SEQ ID NO: 11 with c10orf99 having the amino acid sequence of SEQ ID NO:2 or SEQ ID NO:6 in the presence and absence of a candidate modulator under conditions permitting the binding of said c10orf99 to said GPR15; and
   (b) measuring the binding of said GPR15 to said c10orf99, wherein a decrease in binding in the presence of said candidate modulator, relative to the binding in the absence of said candidate modulator, identifies said candidate modulator as an agent that modulates the function of binding between c10orf99 and GPR15.

3. A method of identifying an agent that modulates the signaling activity of GPR15, said method comprising:
   (a) contacting GPR15 having the amino acid sequence of SEQ ID NO: 9, SEQ ID NO: 10 or SEQ ID NO: 11 with c10orf99 having the amino acid sequence of SEQ ID NO:2 or SEQ ID NO:6 in the presence and absence of a candidate modulator; and
   (b) measuring a signaling activity of said GPR15, wherein a change in the signaling activity in the presence of said candidate modulator relative to the signaling activity in the absence of said candidate modulator identifies said candidate modulator as an agent that modulates the signaling activity of GPR15.

4. A method of identifying an agent that increases the signaling activity of GPR15, said method comprising:
   (a) contacting GPR15 having the amino acid sequence of SEQ ID NO: 9, SEQ ID NO: 10 or SEQ ID NO: 11 with a candidate modulator;
   (b) measuring a signaling activity of said GPR15 in the presence of said candidate modulator; and
   (c) comparing said signaling activity measured in the presence of said candidate modulator to said signaling activity measured in a sample in which said GPR15 is contacted with c10orf99 having the amino acid sequence of SEQ ID NO:2 or SEQ ID NO:6 at its $EC_{50}$, wherein said candidate modulator is identified as an agent that increases the signaling activity of GPR15 when the amount of said signaling activity measured in the presence of said candidate modulator is at least 50% of the amount induced by said c10orf99 present at its $EC_{50}$.

5. The method of claim 3 or 4, wherein the step of measuring a signaling activity comprises (i) detecting a change in the level of a second messenger, said second messenger being cAMP or intracellular calcium, or (ii) measuring guanine nucleotide binding or exchange, adenylatecyclase activity, Protein Kinase C activity, phosphatidylinositol breakdown, diacylglycerol, inositol triphosphate, arachinoid acid, MAP kinase activity, tyrosine kinase activity, or reporter gene expression.

\* \* \* \* \*